(12) United States Patent
Sondermann et al.

(10) Patent No.: US 7,074,896 B1
(45) Date of Patent: Jul. 11, 2006

(54) RECOMBINANT SOLUBLE FC RECEPTORS

(75) Inventors: Peter Sondermann, Krailling (DE); Robert Huber, Germering (DE); Uwe Jacob, München (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 09/856,933

(22) PCT Filed: Dec. 3, 1999

(86) PCT No.: PCT/EP99/09440

§ 371 (c)(1),
(2), (4) Date: Feb. 27, 2002

(87) PCT Pub. No.: WO00/32767

PCT Pub. Date: Jun. 8, 2000

(30) Foreign Application Priority Data

Dec. 3, 1998 (EP) .................................. 98122969

(51) Int. Cl.
*C07K 14/00* (2006.01)
*A61K 39/00* (2006.01)

(52) U.S. Cl. ..................................... 530/350; 424/185.1
(58) Field of Classification Search ................ 530/350; 424/185.1
See application file for complete search history.

(56) References Cited

U.S. PATENT DOCUMENTS

| 5,470,578 A | * | 11/1995 | Aoki et al. | ................ | 424/450 |
| 5,623,053 A | * | 4/1997 | Gastinel et al. | ............ | 530/350 |
| 6,675,105 B1 | * | 1/2004 | Hogarth et al. | .............. | 702/27 |

FOREIGN PATENT DOCUMENTS

| EP | 0 259 615 | 3/1988 |
| EP | 0 321 842 | 5/1989 |
| EP | 0614978 A1 * | 8/1994 |
| EP | 0 614 978 | 9/1994 |
| EP | 0 791 653 | 8/1997 |
| FR | 2 739 560 | 4/1997 |
| WO | 95 09002 | 4/1995 |
| WO | 96 40199 | 12/1996 |
| WO | 99 05271 | 2/1999 |

OTHER PUBLICATIONS

Feldman et al., Transplant. Proc. 1998, 30, 4126-4127.*
Cochlovius et al., Modern Drug Discovery, 2003, pp. 33-38.*
Mikayama et al. PNAS, 1993, 90: 10056-10060.*
Burgess et al., J Cell Biol. 111:2129-2138, 1990.*
Lazar et al., Mol Cell Biol. 8:1247-1252, 1988.*
Jerome Galon et al., "Ligands and Biological Activities of Soluble Fcgamma Receptors", *Immunology Letters*, 44:175-181 (Jan. 1995).
Janet M. Allen et al., "Isolation and Expression of Functional High-Affinity Fc Receptor Complementary DNAs", *Journal of Crystal Growth*, 93:1-4:378-381 (Nov. 1988-Dec. 1988).
Wilhelm P. Burmeister et al., "Crystal Structure at 2.2A Resolution of the MHC-Related Neonatal Fc Receptor", *Nature*, 372:6504:336-343 (Nov. 1994).

* cited by examiner

*Primary Examiner*—Christina Chan
*Assistant Examiner*—Michail A. Belyavskyi
(74) *Attorney, Agent, or Firm*—Fulbright & Jaworski L.L.P.

(57) ABSTRACT

Recombinant soluble Fc receptors according to the present invention are characterized by the absence of transmembrane domains, signal peptides and glycosylation. Such Fc receptors can easily be obtained by expressing respective nucleic acids in prokaryotic host cells and renaturation of the obtained inclusion bodies, which procedure leads to a very homogenous and pure product. The products can be used for diagnostic as well as pharmaceutical applications and also for the generation of crystal structure data. Such crystal structure data can be used for the modelling of artificial molecules. A further embodiment comprises coupling the Fc receptors according to the invention to solid materials like chromatography materials that can be used to separate and/or enrich antibodies.

2 Claims, 10 Drawing Sheets

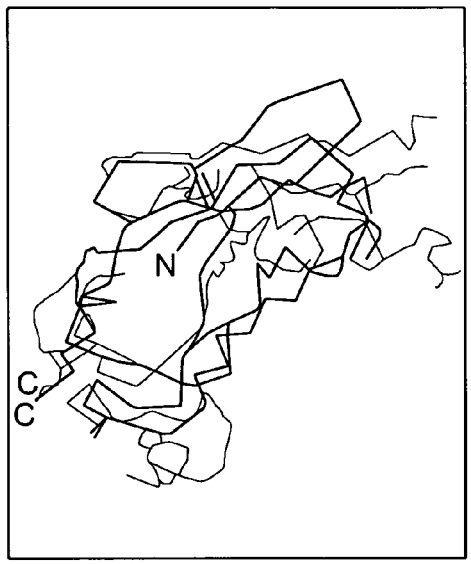 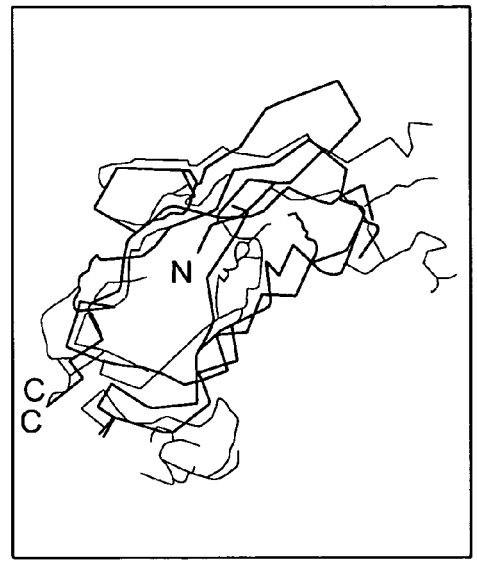
FIG. 5A
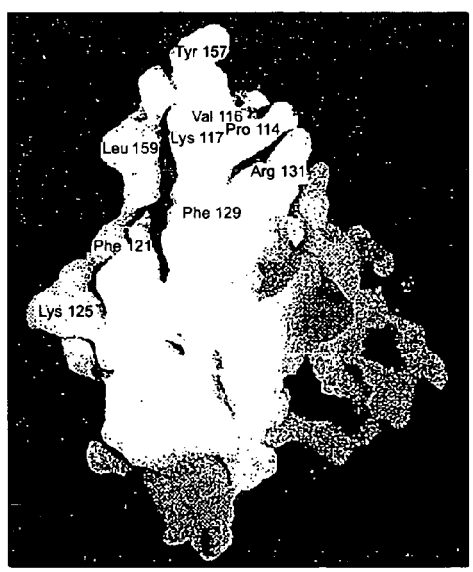 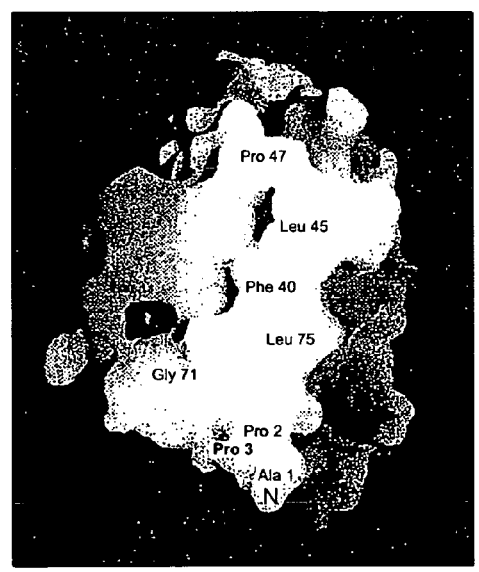
FIG. 6A FIG. 6B

Alignment of the Produced sFcγR, sFcεRIa and the short form of sFcεRII

```
sFcγRIIa    ---MAAPPKAVLKLEPP-WINVLQEDSVTLTCQGARSPESDSIQWFHN-GNLIPTHTQPS   55
sFcγRIIb    MGTPAAPPKAVLKLEPQ-WINVLQEDSVTLTCRGTHSPESDSIQWFHN-GNLIPTHTQPS   58
sFcγRIII    -MRTEDLPKAVVFLEPQ-WYSVLEKDSVTLKCQGAYSPEDNSTQWFHN-ESLISSQASSY   57
sFcγRI      --------MAVISLQPP-WVSVFQEETVTLHCEVLHLPGSSSTQWFLN-GTATQTSTPSY   50
sFcεRIa     ---MAVPQKPKVSLNPP-WNRIFKGENVTLTCNGNNFFEVSSTKWFHN-GSLSEETNSSL   55
sFcεRII     -MELQVSSGFVCNTCPEKWINFQRK------C---YYFGKGTKQWVHARYACDDMEGQLV   50
                      *    *     . .  :      *          .:  :*.

sFcγRIIa    YRFKANNNDSG-EYTCQTGQTSLSDPVHLTVLSEWLV-LQTPHLEFQEGETIMLRCHSWK   113
sFcγRIIb    YRFKANNNDSG-EYTCQTGQTSLSDPVHLTVLSEWLV-LQTPHLEFQEGETIVLRCHSWK   116
sFcγRIII    FIDAATVNDSG-EYRCQTNLSTLSDPVQLEVHIGWLL-LQAPRWVFKEEDPIHLRCHSWK   115
sFcγRI      RITSASVNDSG-EYRCQRGLSGRSDPIQLEIHRGWLL-LQVSSRVFTEGEPLALRCHAWK   108
sFcεRIa     NIVNAKFEDSG-EYKCQHQQVNESEPVYLEVFSDWLL-LQASAEVVMEGQPLFLRCHGWR   113
sFcεRII     SIHSPEEQDFLTKHASHTGSWIGLRNLDLKGEFIWVDGSHVDYSNWAPGEPTS-RSQGED   109
               . :*   ::.:         : *     *:   :.          :.   *..

sFcγRIIa    DKPLVKVTFFQNGK-SQKFSRLDPTFSIPQANHSHSGDYHCTGNIGYTLFSSKPVTITVQ   172
sFcγRIIb    DKPLVKVTFFQNGK-SKKFSRSDPNFSIPQANHSHSGDYHCTGNIGYTLYSSKPVTITVQ   175
sFcγRIII    NTALHKVTYLQNGK-DRKYFHHNSDFHIPKATLKDSGSYFCRGLVGSKNVSSETVNITIT   174
sFcγRI      DKLVYNVLYYRNGK-AFKFFHWNSNLTILKTNISHNGTYHCSG-MGKHRYTSAGISVTVK   166
sFcεRIa     NWDVYKVIYYKDGE-ALKYWYENHNISITNATVEDSGTYYCTGKVWQLDYESEPLNITVI   172
sFcεRII     CVMMRGSGRWNDAFCDRKLGAWVCDRLATCTPPASEGSAESMGPDSRPDPDGRLPTPSAP   169
                   :        .:.  *           :  .*  . *             . :

sFcγRIIa    VP----------------------------------------------------------  174
sFcγRIIb    APSSSPMGII--------------------------------------------------  185
sFcγRIII    QG----------------------------------------------------------  176
sFcγRI      ELFPAPVLNASVTSPLLEGNLVTLSCETKLLLQRPGLQLYFSFYMGSKTLRGRNTSSEYQ   226
sFcεRIa     KAPREKYWLQF-------------------------------------------------  183
sFcεRII     LHS---------------------------------------------------------  172 sFcγRIIa    ------------------------------------------
sFcγRIIb    ------------------------------------------
sFcγRIII    ------------------------------------------
sFcγRI      ILTARREDSGLYWCEAATEDGNVLKRSPELELQVLGLQLPTPV   269
sFcεRIa     ------------------------------------------
sFcεRII     ------------------------------------------
```

FIG. 11

Alignment the Produced sFcγR and sFcεRIa without sFcεRII

```
sFcγRIIa    ---MAAPPKAVLKLEPPWINVLQEDSVTLTCQGARSPESDSIQWFHNGNLIPTHTQPSYR   57
sFcγRIIb    MGTPAAPPKAVLKLEPQWINVLQEDSVTLTCRGTHSPESDSIQWFHNGNLIPTHTQPSYR   60
sFcγRIII    -MRTEDLPKAVVFLEPQWYSVLEKDSVTLKCQGAYSPEDNSTQWFHNESLISSQASSYFI   59
sFcγRI      --------MAVISLQPPWVSVFQEETVTLHCEVLHLPGSSSTQWFLNGTATQTSTPSYRI   52
sFcεRIa     ---MAVPQKPKVSLNPPWNRIFKGENVTLTCNGNNFFEVSSTKWFHNGSLSEETNSSLNI   57
                 . :*.* *  ::: :.*** *.      .* .** * .          .

sFcγRIIa    FKANNNDSGEYTCQTGQTSLSDPVHLTVLSEWLVLQTPHLEFQEGETIMLRCHSWKDKPL   117
sFcγRIIb    FKANNNDSGEYTCQTGQTSLSDPVHLTVLSEWLVLQTPHLEFQEGETIVLRCHSWKDKPL   120
sFcγRIII    DAATVNDSGEYRCQTNLSTLSDPVQLEVHIGWLLLQAPRWVFKEEDPIHLRCHSWKNTAL   119
sFcγRI      TSASVNDSGEYRCQRGLSGRSDPIQLEIHRGWLLLQVSSRVFTEGEPLALRCHAWKDKLV   112
sFcεRIa     VNAKFEDSGEYKCQHQQVNESEPVYLEVFSDWLLLQASAEVVMEGQPLFLRCHGWRNWDV   117
             *. :***** **      *:*: *  :  **.**..    * :.: ****.*:: :

sFcγRIIa    VKVTFFQNGKSQKFSRLDPTFSIPQANHSHSGDYHCTGNIGYTLFSSKPVTITVQVP---   174
sFcγRIIb    VKVTFFQNGKSKKFSRSDPNFSIPQANHSHSGDYHCTGNIGYTLYSSKPVTITVQAPSSS   180
sFcγRIII    HKVTYLQNGKDRKYFHHNSDFHIPKATLKDSGSYFCRGLVGSKNVSSETVNITITQG---   176
sFcγRI      YNVLYYRNGKAFKFFHWNSNLTILKTNISHNGTYHCSG-MGKHRYTSAGISVTVKELFPA   171
sFcεRIa     YKVIYYKDGEALKYWYENHNISITNATVEDSGTYYCTGKVWQLDYESEPLNITVIKAPRE   177
             :*  : ::*: *:    : : *::. ...* *.* *    *  :..*:

sFcγRIIa    ------------------------------------------------------------
sFcγRIIb    PMGII------------------------------------------------------   185
sFcγRIII    ------------------------------------------------------------
sFcγRI      PVLNASVTSPLLEGNLVTLSCETKLLLQRPGLQLYFSFYMGSKTLRGRNTSSEYQILTAR   231
sFcεRIa     KYWLQF-----------------------------------------------------   183 sFcγRIIa    -------------------------------------
sFcγRIIb    -------------------------------------
sFcγRIII    -------------------------------------
sFcγRI      REDSGLYWCEAATEDGNVLKRSPELELQVLGLQLPTPV   269
sFcεRIa     -------------------------------------
```

FIG. 12

RECOMBINANT SOLUBLE FC RECEPTORS

The present invention relates to recombinant soluble Fc receptors (FcR), recombinant nucleic acids coding for such Fc receptors, host cells containing corresponding nucleic acids as well as a process for the determination of the amount of antibodies of a certain type contained in the blood, plasma or serum of a patient, a process for the determination of the immune status of patients with chronic diseases of the immune system and a process for the screening of substances in view of their ability to act as inhibitors of the recognition and binding of antibodies to the respective cellular receptors. Further, the present invention is concerned with pharmaceutical compositions containing the recombinant soluble FcRs, crystalline preparations of FcRs and FcR/Ig-complexes and especially of the use of such crystalline preparation for the generation of crystal structure data of Fc receptors as well as FcR inhibitors and pharmaceutical compositions containing such FcR inhibitors.

A still further subject of the present invention is a recombinant Fc receptor coupled to a solid phase, e.g. a chromatography carrier material. The use of such chromatography material, which is another subject of the present invention, lies in the absorption of immunoglobulins from a body fluid of patients or from culture supernatants of immunoglobulin producing cells.

Fc receptors (FcRs) play a key role in defending the human organism against infections. After pathogens have gained access to the blood circulation they are opsonized by immunoglobulins (Igs). The resulting immunocomplexes bind due to their multivalency with high avidity to FcR bearing cells leading to clustering of the FcRs, which triggers several effector functions (Metzger, H., 1992A). These include, depending on the expressed FcR type and associated proteins, endocytosis with subsequent neutralization of the pathogens and antigen presentation, antibody-dependent cellular cytotoxity (ADCC), secretion of mediators or the regulation of antibody production (Fridman et al, 1992; van de Winkel and Capel, 1993).

Specific FcRs exist for all Ig classes, the ones for IgG being the most abundant with the widest diversity. Together with the high affinity receptor for IgE (FcεRIa), FcγRI (CD64), FcγRII (CD32) and FcγRIIIa (CD16) occur as type I transmembrane proteins or in soluble forms (sFcRs) but also a glycosylphosphatidylinositol anchored form of the FcγRIII (FcγRIIIb) exists. Furthermore, FcγRs occur in various isoforms (FcγRIa, b1, b2, c; FcγRIIa1-2, b1-3, c) and alleles (FcγRIIa1-HR, -LR; FcγRIIIb-NA1, -NA2) (van de Winkel and Capel, 1993). In contrast to the overall homologous extracellular parts, the membrane spanning and the cytoplasmic domains differ. They may be deleted entirely or be of a size of 8 kDa. They may contain either a 26 amino acid immunoreceptor tyrosine-based activation motif (ITAM) as in FcγRIIa or a respective 13 amino acid inhibitory motif (ITIM) in FcγRIIb involved in signal transduction (Amigorena et al, 1992).

Judged by the conserved spacing of cysteins, the extracellular part of the FcRs consists of three (FcγRI, CD64) or two (FcεRI, FcγRII, CD32 and FcγRIII, CD16) Ig-like domains (10 kDa/domain) and therefore belongs to the immunoglobulin super family. These highly glycosylated receptors are homologues, and the overall identity in amino acid sequence among the FcγRs and FcεRIa exceeds 50% in their extracellular regions. Nevertheless, the affinity of FcRs to their ligands varies widely. The higher affinity of $\approx 10^8 M^{-1}$ of the FcγRI to Fc-fragment is assigned to its third domain, while the other FcγRs with two domains have an affinity to IgG varying between $10^5$ and $10^7 M^{-1}$. The affinity of the two domain FcεRIa to IgE exceeds these values by far with a constant of $10^{10} M^{-1}$ (Metzger, H., 1992B). In contrast to the mentioned FcRs the low affinity receptor for IgE FcεRII represents a type transmembrane protein and shows a lower homology.

FcγRs are expressed in a defined pattern on all immunological active cells. FcγRI is constitutively expressed on monocytes and macrophages and can be induced on neutrophils and eosinophils. The physiological role of FcγRI is still unknown as the expression on monocytes is not vital (Ceuppens et al, 1988). The GPI anchored form of FcγRIII (FcγRIIIb) is exclusively expressed on granulocytes. Due to its missing cytoplasmic part, the signal transduction into the cell occurs solely via other transmembrane proteins like complement receptor type 3 (CR3) that can at least associate with FcγRIIIb (Zhou et al, 1993; Poo et al, 1995). FcγRIIIa is mainly expressed on monocytes and macrophages but only in conjunction with associated proteins (e.g. α- or γ-chains). FcγRII is the receptor with the widest distribution on immunocompetent cells and is mainly involved in the endocytosis of immunocomplexes.

FcγRIIa and FcγRIIb differ in their extracellular region by only 7% of the amino acid residues. Nevertheless, both forms can be distinguished by their binding characteristics to human and mouse IgG subclasses (van de Winkel and Capel, 1993) and their differing affinity to human IgGs (Sondermann et al, 1998A). The situation is rendered even more complicated by the high responder/low responder (HR/LR) polymorphism of FcγRIIa named after the ability of T cells from some individuals to respond to murine IgG 1-induced mitogenesis (Tax et al, 1983). Later, it was found that the two exchanges in the amino acid sequence between the LR and the HR form modify the ability to bind human IgG2, which leads to the suggestion that at least one of them is involved in IgG binding (Hogarth et al, 1992).

In contrast to the beneficial role FcRs play in the healthy individual, they also transmit the stimulation of the immune system in allergies (FcεRIa) or autoimmune diseases. Moreover, some viruses employ FcγRs to get access to cells like HIV (Homsy et al, 1989) and Dengue (Littaua et al, 1990) or slow down the immune response by blocking FcγRs as in the case of Ebola (Yang et al, 1998) and Measles (Ravanel et al, 1997).

Hence, the object underlying the present invention was to provide receptors which are easy to produce and can advantageously be used for medical or diagnostic applications. Moreover, it was an object of the invention to provide soluble receptors exhibiting a binding specificity and activity which is analogous to that of the receptors occurring naturally in the human body and which, additionally, make it possible to produce crystals suitable for a structure determination.

This object is accomplished by recombinant soluble Fc receptors which consist only of the extracellular portion of the receptor and are not glycosylated. The receptors according to the present invention are therefore characterized by the absence of transmembrane domains, signal peptides and glycosylation.

Particularly preferred for the present invention are Fcγ or Fcε receptors. This is because IgG and IgE molecules are characteristic for a multiplicity of diseases and conditions, so that their determination and possible ways of influencing them are of great interest. FIGS. 11 and 12 show an alignment of amino acid sequences of the extracellular parts of some FcγRs and FcεRI. The FcRs according to the invention include all these sequences or parts thereof that still retain binding capacity to antibodies and/or proper crystallization.

In a particularly preferred embodiment of the invention the recombinant soluble FcR is a FcγRIIb receptor. Further, it is particularly preferred that the receptor be of human origin. In a particularly preferred embodiment, it contains an amino acid sequence as shown in one of SEQ ID NO:1 to SEQ ID NO:6.

According to the present invention, the preparation of the soluble Fc receptors preferably takes place in prokaryotic cells. After such expression, insoluble inclusion bodies containing the recombinant protein form in prokaryotic cells, thus facilitating purification by separation of the inclusion bodies from other cell components before renaturation of the proteins contained therein takes place. The renaturation of the FcRs according to the present invention which are contained in the inclusion bodies can principally take place according to known methods. The advantage of the preparation in prokaryotic cells, the production of inclusion bodies and the thus obtained recombinant soluble Fc receptors make it possible to obtain a very pure and, in particular, also very homogeneous FcR preparation. Also because of the absence of glycosylation the obtained product is of great homogeneity.

Soluble Fc receptors hitherto produced by recombinant means particularly exhibited the disadvantage that a much more elaborate purification was required, since they were expressed in eukaryotic cells and, due to the glycosylation which is not always uniform in eukaryotic cells, these products were also less homogeneous.

The recombinant soluble Fc receptors according to the present invention even make it possible to produce crystals suitable for use in X-ray analysis, as shall be explained later on in the description of further embodiments of the invention. The FcRs of the present invention moreover exhibit practically the same activity and specificity as the receptors naturally occurring in vivo.

A further subject matter of the present invention is a recombinant nucleic acid having a sequence coding for a recombinant soluble Fc receptor according to the present invention.

The nucleic acid according to the present invention may contain only the coding sequences or, additionally, vector sequences and/or, in particular, expression control sequences operatively linked to the sequence encoding the recombinant FcR, like promoters, operators and the like.

In a particularly preferred embodiment the nucleic acid of the present invention contains a sequence as shown in one of SEQ ID NO:7 to SEQ ID NO:12. For a comparison, SEQ ID NO:13 and SEQ ID NO:14 show the respective wild type sequences coding for FcγRIIb and FcεRIa. SEQ ID NOs: 15–18 show the wild type sequences for FcγRI, FcγRIIa, FcγRIII and FcεRII.

If the nucleic acid of the present invention contains vector sequences, then these are preferably sequences of one or several prokaryotic expression vectors, preferably of pET vectors. Any other known functions or components of expression vectors may also be contained in the recombinant nucleic acid according to the present invention if desired. These may, for instance, be resistance genes allowing for an effective selection of transformed host cells.

A still further subject matter of the present invention is a host cell containing a recombinant nucleic acid according to the present invention. As repeatedly mentioned above, the host cell preferably is a prokaryotic host cell, particularly an E. coli cell.

The recombinant soluble Fc receptors according to the present invention can be used for a multitude of examinations or applications because they specifically react with antibodies. In vivo, the soluble Fc receptors are powerful immunoregulators which, if present in elevated levels, result in a remarkable suppression of the immune system which leads to many partly known and partly not yet understood effects. Based on these effects, several applications of the Fc receptors according to the present invention are further subject matters of the present invention.

One such subject is a process for the determination of the amount of antibodies of a certain type in the blood or serum of a patient, which is characterized by the use of a recombinant soluble FcR according to the invention in an immunoassay, and the determination of the presence of FcR-antibody complexes. Such assay allows to screen for the presence of a certain kind of antibody and allows also for the determination of the amount of antibodies present in the blood, plasma or serum of a patient.

Any type of immunoassay is principally suitable for the use according to the present invention, as long as the presence of FcR-antibody complexes can thereby be detected. Both ELISA (enzyme-linked immunosorbent immunoassay), particularly sandwich assays, and RIA (radio-immunoassay) are suitable, but also competitive testing methods. In a preferred embodiment of the invention where the presence and/or the amount of IgE antibodies is to be examined, an FcεR is used as recombinant soluble receptor according to the present invention. In particular, this method is suited and advantageous for determining a predisposition or manifestation of an allergy.

Moreover, a method is preferred in which the presence of soluble FcRs is to be determined and, if required, quantified. For such determination preferably a competitive immunoassay method is used, wherein as competition reagent a recombinant soluble receptor according to the invention is used, most preferably a recombinant FcγR. By means of this test among others the immune status of patients with chronic diseases of the immune system can be determined in a competitive immunoassay. Chronic diseases in the sense of these processes are for instance AIDS, SLE (systemic lupus erythematosus), MM (multiple myeloma) or rheumatoid arthritis, or in the case of FcεRII in B-CLL (Gordon et al., 1987), hyper IgE syndrome (Sarfati et al., 1988) or HCL (Small et al., 1990).

A further advantageous use of the recombinant receptor according to the present invention lies in the screening of substances in view of their ability to act as inhibitors of the recognition and binding of antibodies to the respective cellular receptors.

By means of modern screening techniques such as HTPS (high throughput screening) in combination with multi-well microtiter plates and automatic pipetting apparatuses it is nowadays possible to simultaneously test a multitude of substances for specific properties. As the FcRs according to the present invention can be easily produced at low cost, they can also be used in such series tests by which substances having an inhibiting effect can easily be identified.

Particularly preferred is such use according to which Fc receptors according to the present invention are used to find or screen inhibitors capable of inhibiting the recognition and binding of the respective antibodies to the particular receptor of interest.

A further area of application of the substances according to the invention lies in the pharmaceutical field. Hence, a further subject matter of the invention is a pharmaceutical composition comprising as active agent a recombinant soluble FcR according to the invention. According to the present invention, this pharmaceutical composition may of course comprise conventional useful carrier and auxiliary substances. Such substances are known to the person of skill in the art, the mode of administration also having to be taken into account. The pharmaceutical composition of the present invention can be advantageously used for the treatment or prevention of autoimmune diseases, allergies or tumor diseases.

Soluble forms of Fc receptors such as FcγRIII mediate isotype-specific regulation of B cell growth and immunoglobulin production. In a murine model of myeloma, sFcR suppresses growth and immunoglobulin production of tumor cells (Müller et al, 1985; Roman et al, 1988; Teillaud et al, 1990). Furthermore, sFcR binds to surface IgG on cultures of human IgG-secreting myeloma cells and effects suppression of tumor cell growth and IgG secretion. Prolonged exposure of these cells to sFcR results in tumor cell cytolysis (Hoover et al, 1995).

Also, overreactions of the immune system in allergic reactions or due to massive antigen load might be reduced by, for example, intravenous application of soluble FcR (Ierino et al, 1993).

Therefore, a preferred pharmaceutical composition according to the invention for use in the treatment of AIDS, rheumatoid arthritis or multiple myeloma contains a recombinant soluble Fcγ receptor and, preferably, a receptor having the amino acid sequence as shown in SEQ ID NO:1–4.

It was also of great interest to obtain crystal structure data of Fc receptors and/or Fc receptor/Ig complexes. On the one hand, these are a key to the understanding of molecular mechanisms in immunocomplex recognition. On the other hand, these structural data can be used to find out common features in the structures of different Fc receptors and use the knowledge of the structures to generate inhibitors or identify and produce new artificial antibody receptors.

It was also of great interest to obtain information on the concrete binding sites of immunoglobulins to their respective receptors in naturally occuring three-dimensional molecules. Therefrom even more precise findings on the interactions between antibody and receptor can be obtained and also on how these interactions can be modulated. In this connection modulation means either an enhancement of the interaction or a reduction leading to an inhibition by e.g. covering the binding sites on one or more parts of the complex.

To obtain such crystal structure data and conformation information, a crystalline preparation of the recombinant soluble Fc receptor according to the invention is used. The recombinant soluble FcRs according to the invention surprisingly can be obtained pure enough to produce crystals that give reliable X-ray structure determination data. Such crystallization was not possible with the hitherto produced receptor molecules, mostly due to their lack of homogeneity.

Therefore, another embodiment of the present invention concerns a crytalline preparation of an Fc receptor according to the invention. Yet another embodiment of the present invention is a crystalline preparation of a complex of soluble Fc receptor according to the invention together with the related immunoglobulin Fc part. Particulary preferred embodiments are shown in the examples as well as the relevant crystal structure data. Via crystal structure analysis of the crystalline preparations the exact amino acids of the Fc receptor/Ig complexes could be detected which mediate the coupling. These amino acids are in shown FIGS. 6a and 6b and the type of binding between the individual amino acids of both molecules in the complex is also indicated. A further embodiment of the present invention is therefore the use of a crystalline preparation of a recombinant soluble Fc receptor for the generation of crystal structure data of Fc receptors. From this crystal structure data information about the three-dimensional structure and the active sites for the binding of antibodies can be obtained. Especially preferably is the use of a crystalline preparation of a complex of recombinant soluble Fc receptor according to the invention and the corresponding immunoglobulin molecule for the generation of crystal structure data for the complexes. These data allow to determine the actual interactions that are formed between the two molecules and allow for the first time to obtain exact information about the interaction of the molecules thereby conferring knowledge about possible sites for inhibition or enhancement of the binding. On the basis of the information obtained from the crystal structure data the findings necessary for effecting modulation of the interaction between Fc receptor and immunoglobulin can be obtained. This modulation can be range from enhancement to complete inhibition to an inhibition of the binding.

The stated applications are merely preferred embodiments of the use of the crystal structure data. Many other applications seem possible, too.

Suitably, the structural data for the generation and/or identification of inhibitors or new receptors, respectively, are used in a computer-aided modelling program.

Particularly preferred for the present invention are the structures of FcRs or FcR:Fc-fragment complexes as exemplified in figures and examples. Such structures can be used to design inhibitors, antagonists and artificial receptor molecules.

Computer programs suitable for computer-aided drug design and screening are known to the person skilled in the art and generally available. They provide the possibility to examine umpteen compositions on the computer in view of their ability to bind to a certain molecule when the corresponding structure dates are entered in the computer. With the help of this possibility a great number of known chemical compositions can be examined regarding their inhibiting or antagonistic effect. The person skilled in the art merely requires the crystal structure dates provided by the present invention and a commercially available screening program (Program Flexx: From the GMD-German National Research Center for Information Technology, Schloss Birlinghoven, D-53754 Sankt Augustin, Germany). A preferred embodiment of the present invention therefore is the use of the crystal structure data obtained for the recombinant soluble Fc receptor according to the invention and for the complexes of recombinant soluble Fc receptor according to the invention and corresponding immunoglobulin in a computer aided modelling program for the identification and production of Fc receptor inhibitors.

Likewise, a further embodiment of the present invention is the use of the crystal structure data obtained for the receptors according to the invention and the receptor/immunoglobulin complexes, respectively for the identification and preparation of new Fc receptors which can be used, e.g. as antagonists and competitors. The crystal structure data and the data on the amino acids involved in the binding to Fc receptors obtained therefrom can serve for example to generate mutated immunoglobulins which can also be used as inhibitors. It is imaginable that mutated or chemically modified inhibitors undergo tight binding and thus effect a blocking of receptors. On the other hand, the data obtained for the binding sites of immunoglobulins can also be used for the identification and/or preparation of inhibitors for immunoglobulin molecules. Since the present invention teaches the binding sites to the receptor, it is easy to effect a blocking of the binding sites with the help of relatively simple molecules. Therefore, a further subject matter of the present invention is the use of the crystal structure data obtained for the FcR/Ig complexes for the identification and/or preparation of immunoglobulin inhibitors.

Accordingly, still further subject matter of the present invention are FcR inhibitors which have a three-dimensional structure which is complementary to the recombinant soluble FcR according to the invention and inhibit the binding of antibodies to FcRs.

Another further subject of the present invention are immunoglobulin inhibitors which have a three-dimensional structure which is complementary to the immunoglobulin binding site for recombinant soluble Fc receptors according to the invention and inhibit the binding of immunoglobulins to Fc receptors.

The term "complementary" is to be understood within the framework of the invention in such a way that the inhibitor molecules must be substances which are able to cover at least so many binding sites on the immunoglobulin or on the Fc receptor that the binding between Fc receptor and immunoglobulin is at least decisively weakened. Covering can take place both by binding to the amino acids mediating the complex formation of either component but also in such a way that at least complex formation is no longer possible, be it by sterically inhibition or by binding to adjacent amino acids, however, covering the amino acid involved in the complex binding between Fc receptor and immunoglobulin.

In connection with the present invention it was possible for the first time to determine the exact binding sites and the amino acids involved in the binding of the antibody and antibody receptor molecules. One is now able to design specifically binding molecules and to screen candidate compositions on the computer. This enables the selection of such compositions from a variety of possibly candidate compositions which can effect a sufficient inhibition of complex formation between Fc receptor and immunoglobulin.

What is important for the inhibitors of the invention is that, owing to their structure and specificity, they are capable of binding to the FcRs or immunoglobulins and thus prevent the normal binding between FcRs and the constant parts of antibodies.

Preferably, such FcR or IgG inhibitors are small organic molecules which can easily be administered orally. They are an interesting alternative to cortisone in the treatment of autoimmune diseases and host/graft rejections. Such a molecule would also suppress reinfection rates with certain viruses, e.g. Dengue virus where the antibody coated virus is FcγRIIb dependent internalized (Littaua et al, 1990), HIV where on CD4 positive T cells an antibody enhancement of HIV infection is mediated by FcγRIII (Homsy et al, 1989), or Ebola where the virus secreted glycoprotein inhibits early neutrophil activation by blocking sFcγRIII which affects the host response to infection (Yang et al, 1998).

The development of inhibitors also leads to substances that interfere with the recognition of IgE by their receptors. From the modelled structure of FcεRI, peptides have already been developed which inhibit mast cell degranulation in vitro. With the now available knowledge of the structures of the homologue receptors and the receptor-antibody complex in atomic detail, a new possibility for a rational drug design is opened.

The Fc-receptor bind between the two CH2-domains of the Fc-fragment in the so-called lower hinge region (FIG. 8). The binding region of the Fc-receptor is described in Example 1 (The contact interface to IgG). The residues promoting the interaction between FcR and immunoglobulin are shown in FIGS. 7, 10*a* and 10*b*. Thereby three interaction regions become evident (FIG. 5).

1st Region: FcR (Residues 85 to 87 and Residue 110)-Ig (Chain A Residues 326–328)

Proline 328 of the Ig is clamped by the residues Trp 87 and 110 in a sandwich like manner. These residues are conserved among the IgG and IgE receptors as well as in the IgG and IgE. An inhibitor binding to this prominent region would strongly interfere with binding. This region is additionally attractive for inhibitor design because the exposed hydrophobic surface region comprising the residues Trp 87, Ile 85, Gly 86 of the receptors could be employed to obtain additional binding energy. The functional groups of Thr 113 and Glu 18 and Lys 19 side chains in the vicinity may contribute especially to specific inhibitor binding.

2nd Region: FcR (Residues 126–132 and Residues 155–158)-Ig (Chain A and Chain B Residues 234–239)

The amino terminal residues 234–239 of both Ig chains are recognised differently by the FcR, thereby breaking the 2-fold symmetry of the Fc fragment.

This residues of Fc-fragment chain A are in contact with residues Val 155-Lys 158 of the receptor and the same residues from Fc-fragment chain B with receptor residues Gly 126–His 132. This region shows the most differences in the sequence alignment of the receptors as well as the immunoglobulins and should therefore be involved in specificity generation. This deep cleft between the Fc-fragment chains is well suited for inhibitor design and would be the site of choice for the development of inhibitors when issues of specificity are concerned.

3rd Region: FcR (Residues 117, 126 and 129–132)-Ig (Chain B Residues 264–265 and Residues 296–297)

This binding region is characterised by a clustering of amino acid residues carrying functional groups in their side chains, that might be employed in various ways for inhibitor design on the receptor and the Ig side of the contact.

Molecules that interact with one or more of the above described regions, and are designed or screened explicitly for exploiting the knowledge of binding sites are considered as inhibitors according to the invention.

Further subject matters of the present invention are pharmaceutical compositions containing as active agent an FcR inhibitor or an immunoglobulin inhibitor as mentioned above. Such pharmaceutical compositions may, for example, be used in the treatment or prevention of diseases which are due to overreactions or faulty reactions of the immune system, preferably the treatment or prevention of allergies, autoimmune diseases or anaphylactic shock.

A further subject of the present invention is the sFcR according to the invention, bound to a solid phase. Such heterogeneous receptors can be used for immunoassays or other applications where the receptor in an immobilized form can be used beneficially.

In a preferred embodiment of the invention the solid phase is a chromatography carrier material onto which the Fc receptor is fixed, e.g. sepharose, dextransulfate etc. Such chromatography materials with Fc receptors bound thereto can beneficially be used for the adsorption of immunoglobulins from the blood, plasma or serum of patients or from the culture supernatant of immunoglobulin producing cells (meaning concentration, enrichment and purification of antibodies).

On the one hand, the antibodies bound to the chromatography material can be eluted and, for example, the immune status of a patient can thereby be determined. On the other hand, antibodies from the blood of a patient can thereby be enriched before carrying out further tests, which is a further preferred embodiment of the present invention. In many cases it is difficult to conduct diagnostic assays using blood samples if the latter contains only a very small number of the antibodies to be identified. By means of a concentration using a specific chromatographic column with Fc receptors according to the present invention, antibodies of interest can easily be concentrated and separated from many other substances which might disturb the test.

Basically, it is also possible to use a chromatography material according to the present invention in an extracorporeal perfusion system for ravage of the blood in case of certain diseases where the removal of antibodies plays a crucial role.

It is, however, also possible to use another material as solid phase to which the soluble Fc receptor according to the invention is coupled, e.g. microtiter plates or small reaction vessels to the walls of which Fc receptors are bound either directly or indirectly. Such solid phases and vessels can be particularly important for diagnostic methods, as they enable screening by using immunoassays e.g. for detecting the presence of certain immunoglobins in patients' blood or other body fluids.

To sum up, the recombinant soluble Fc receptors provided by the present invention as well as the corresponding structure determination of crystalline preparations of these receptors and of crystalline complexes of receptors and immunoglobins enable for the first time to perform a rational drug design, wherefrom it is possible to modulate the interaction between immunoglobulins and Fc receptors on cells or soluble receptors. Such a modulation is preferably an inhibition, whereby the inhibition of the formation of a complex from IgG and Fc receptor takes place by covering and preferably by binding of inhibitor molecules to the Fc receptor or the immunoglobulin. There are various medical applications for such modulating drugs and in particular of inhibitors and only few of these applications have been exemplary mentioned within the framework of the present specification. This can and should by no means exclude the applicability of such molecules which have been designed or screened on the basis of the findings about the molecular structure or FcR/Ig complexes disclosed herein for the treatment or prevention of other health disturbances.

The following Examples are to further illustrate the invention in conjunction with the Figures.

EXAMPLE 1 shFcγRIIb (Soluble Human FcγRIIb)

1.1 Cloning and Expression

The cDNA of human FcγRIIb2 (Engelhardt et al, 1990) was modified using mutagenous PCR (Dulau et al, 1989). Therefore, a forward primer was used for the introduction of a new start methionine after the cleavage site of the signal peptide within a NcoI site (5'-AAT AGA ATT CCA TGG GGA CAC CTG CAG CTC CC-3') while the reverse primer introduced a stop codon between the putative extracellular part and the transmembrane region followed by a SalI site (5' CCC AGT GTC GAC AGC CTA AAT GAT CCC C-3'). The PCR product was digested with NcoI and SalI, cloned into a pET11d expression vector (Novagen) and the proposed sequence was confirmed. The final construct was propagated in BL21(DE3) (Grodberg and Dunn, 1988). For the overexpression of FcγRIIb a single colony of the transformed bacteria was inoculated in 5 ml LB medium containing 100 µg ampicillin per ml (LB-Amp100) and incubated overnight at 37° C. The culture was diluted 200-fold in LB-Amp100 and incubation was continued until an OD600 of 0.7–0.9 was achieved. The overproduction of the protein was induced by adding IPTG to a final concentration of 1 mM. After a growing period of 4 hours the cells were harvested by centrifugation (30 min, 4000×g) and resuspended in sonification buffer (30 mM sodium phosphate, 300 mM sodium chloride, 0.02% sodium azide, pH 7.8). After addition of 0.1 mg lysozyme per ml suspension and incubation for 30 min at room temperature the sonification was performed on ice (Branson Sonifier, Danbury, Conn.; Macrotip, 90% output, 80% interval, 15 min). The suspension was centrifuged (30 min, 30,000×g) and resuspended with a Dounce homogenizer in sonification buffer containing 0.5% LDAO. The centrifugation step and resuspension in LDAO containing buffer was repeated once before this procedure was repeated twice without LDAO. The purified inclusion bodies were stored at 4° C.

1.2 Refolding and Purification of Soluble Human FcγRIIb (shFcγRIIb)

The purified inclusion bodies were dissolved to a protein concentration of 10 mg/ml in 6 M guanidine chloride, 100 mM 2-mercaptoethanol and separated from the insoluble matter by centrifugation. The refolding was achieved by rapid dilution. Therefore, one ml of the inclusion body solution was dropped under stirring within 15 hours into 400 ml of the refolding buffer (0.1 M TRIS/HCl, 1.4 M arginine, 150 mM sodium chloride, 5 mM GSH, 0.5 mM GSSG, 0.1 mM PMSF, 0.02% sodium azide, pH 8.5, 4° C.). Afterwards, the mixture was stirred for 2–3 days until the concentration of free thiol groups was reduced to 1 mM by air oxidation as measured according to Ellman (Ellman, 1959). The solution was dialyzed against PBS and sterile filtered before it was concentrated 10-fold in a stirring cell equipped with a 3 kD MWCO ultrafiltration membrane. The protein solution was applied to a hIgG sepharose column (50 mg hIgG per ml sepharose 4B). Unbound protein was washed out with 50 mM TRIS pH 8.0 before elution of FcγRIIb by pH jump (150 mM sodium chloride, 100 mM glycine, 0.02% sodium azide, pH 3.0). The eluate was immediately neutralized with 1 M TRIS pH 8.0. The FcγRIIb containing solution was concentrated and subjected to gel filtration on a Superdex-75 column equilibrated with crystallization buffer (2 mM MOPS 150 mM sodium chloride, 0.02% sodium azide pH 7.0). The fractions containing FcγRIIb were pooled, concentrated to 7 mg/ml and stored at −20° C.

1.3 Equilibrium Gel Filtration Experiments

A Superdex75 column was connected to FPLC and equilibrated with PBS containing 10 µg shFcRIIb per ml. Human Fc fragment was solved to a concentration of 1 µg/10 µl in the equilibration buffer and injected. The resulting chromatogram yielded a positive peak comprising the complex of the shFcγRIIb and the Fc fragment while the negative peak represents the lack of receptor consumed from the running buffer for complex formation.

1.4 Crystallization and Data Collection

Initial crystallization trials employing a 96 condition sparse matrix screen (Jancarik and Kim, 1991) were performed in sitting drops at 20° C. using the vapor diffusion method. Occuring crystals were improved by changing the pH as well as the salt, precipitant and additive concentration. Diffraction data from suitable crystals was collected on an image plate system (MAR research) using graphite monochromated CuK$_\alpha$ radiation from a RU200b rotating anode generator (Rigaku) operated at 50 kV and 100 mA. The reflections were integrated with the program MOSFLM (Leslie, 1997) and subsequently the data was scaled, reduced and truncated to obtain the structure-factor amplitudes using routines from the CCP4 program suite (Collaborative Computational Project, 1994).

1.5 Summary of Expression, Purification and Refolding of shFcγRIIb

The extracellular part of FcγRIIb was expressed in high levels under the control of a T7 promoter in the T7 RNA polymerase positive *E. coli* strand BL21/DE3 (Grodberg & Dunn, 1988). The protein was deposited in inclusion bodies, which were employed in the first purification step. The isolation of the inclusion bodies was started with an intense combined lysozyme/sonification procedure to open virtually all cells which would otherwise contaminate the product. The subsequent washing steps with the detergent LDAO, which has excellent properties in solving impurities but not the inclusion bodies itself already yielded a product with a purity of >90% (FIG. 1).

This product was used for refolding trials without further purification. The inclusion bodies were dissolved in high concentration of 2-mercaptoethanol and guanidine to ensure the shift of covalent and non-covalent aggregates to monomers. This solution was rapidly diluted with refolding buffer to minimize contacts between the unfolded protein molecules which would otherwise form aggregates. The use of arginine in the refolding buffer prevents the irreversible modification of side chains as often recognized with urea. After addition of the protein to the refolding buffer, the solution was stirred at 4° C. until the concentration of free thiol groups was reduced to 1 mM, which was absolutely necessary as earlier dialysis resulted in an inactive product. In a second purification step the dialyzed and refolded FcγRIIb was bound to immobilized hIgG to remove minor fractions of *E. coli* proteins and inactive receptor. The protein was eluted with a pH jump and immediately neutralized. After this affinity chromatography step shFcγRIIb is essentially pure except for a minor contamination resulting from the coeluting IgG which leached out of the matrix even after repeated use (FIG. 1). The IgG as well as receptor multimers which are not visible in the reducing SDS-PAGE could easily be removed by gel filtration. Parallel to the removal of the contaminants in this step the buffer is quantitatively exchanged. This procedure ensures a defined composition of the protein solution as even slight variations can cause irreproducibility of the crystallization attempts or even inhibit the formation of crystals. Overall 6 mg pure protein could be gained per liter *E. coli* culture, which is about 10% from the FcγRIIb content of the inclusion bodies.

N-terminal protein sequencing revealed the identity with the expected sequence H$_2$N-GTPAAP without detectable contamination. ESI-MS analysis showed that the final material used in crystallization trials is homogenous with respect to size. From the primary sequence the molecular weight was calculated to 20434 Da, which corresponds to 20429 Da found by mass spectroscopy. The discrepancy lies within the error of the instrument, and no additional peak for a species containing the leading methionine is found.

The crystallization of shFcγRIIb was performed in sitting drops using the vapor diffusion method. Initial trials with a sparse matrix screen (Jancarik & Kim, 1991) resulted already in small crystalline needles. Subsequent optimization of the preliminary crystallization condition by varying precipitant, salt, their concentration and pH led to the isolation of three different crystal forms. Orthorhombic crystals grew from mixture of 1.5 µl reservoir solution (33% PEG2000, 0.2 M sodium acetate, pH 5.4) with 3 µl of the protein solution. They appeared within 3 days and reached their final size of approximately 80 µm×80 µm×500 µm after one week. These crystals diffracted to 1.7 Å. Crystals could also be grown in two other space groups from reservoir solution containing 26% PEG8000, 0.2 M sodium acetate, pH 5.6, 5 mM Zn(OAc)$_2$, 100 mM sodium chloride (hexagonal form) and 26% PEG8000, 0.2 M NaOAc, pH 5.6, 10% (v/v) 1,4-Dioxan, 100 mM sodium chloride (tetragonal form). These crystals were of suitable size for X-ray analysis but diffracted only to 2.7 Å and 3.8 Å for the tetragonal and hexagonal crystal form respectively (Table 1).

FcγRII was expressed in *E. coli* which, besides the comparatively low production costs and the availability, has several advantages especially when the glycosylation performed by mammalian cells is not necessary for the function of the protein as in the case of FcγRII where IgG binding occurs independently of carbohydrate attachment (Sondermann et al, 1998A). In *E. coli* a homogenous product can reproducibly be generated, which is in contrast to the expression in mammalian cells where batch dependent variances are often observed. In such a system the product is for several days exposed to proteases at temperatures of more than 30° C. In contrary, the expression of the protein in *E. coli* under the control of the strong T7 promoter at 37° C. frequently leads to the formation of protease inaccessible inclusion bodies. A further advantage of the expression in bacteria is that the material could be considered to be free of pathogenic germs, which might derive from employed fetal calf serum or the cell line itself. In mammalian expression particular care must be taken during the purification of the target protein because potential effective hormones or growth factors might be copurified. One case where the effects of sFcγR were ascribed to a TGFβ1 contamination is already reported (Galon et al, 1995).

1.6 Purification

The purification procedure is straightforward. It consists of three steps which can easily be performed in a single day. The protein is obtained in a pure form and in high yields and could even be obtained in considerable quality without the expensive IgG affinity column. The success of such a protocol would depend on the careful preparation of the inclusion bodies, as most of the impurities can be eliminated already in the first purification step.

1.7 Characterization

The purified FcγRIIb was characterized by SDS-PAGE and isoelectric focussing as well as N-terminal sequencing and mass spectroscopy. Thus, the material can be considered pure and homogeneous with respect to its chemical composition, but the intriguing question whether the receptor is correctly folded remains to be discussed. All cysteins are paired, since no free thiol groups are detected with Ellman's test. The material is monomeric and eludes with the expected retention time in peaks of symmetrical shape from a size exclusion chromatography column. Furthermore, FcγRIIb binds to IgG sepharose, recombinant FcγRIIb from *E. coli* is active because it specifically binds IgG.

1.8 Crystallization

The orthorhombic crystal form of FcγRIIb diffracted X-rays to a resolution of 1.7 Å, which is a drastic improvement compared to previously reported crystals of the same molecule derived from insect cell expression (Sondermann et al, 1998A). These crystals diffracted to 2.9 Å and were of space group P3$_1$21. Thus, the glycosylation of the insect cell derived receptor influences the crystallization conditions. Instead of the trigonal space group, three different crystal forms are found. After a possible solution of the structure these crystal forms will help identify artificial conformations of the protein due to crystal contacts.

FcγRs do not exhibit any sequence similarity to other proteins but due to a conserved cystein spacing they are affiliated to the immunoglobulin super family. Consequently, we tried to solve its structure by molecular replacement, but extensive trials using IgG domains from a variety of molecules failed. Thus the structure of FcγRIIb has to be solved by the methods of multiple isomorphous replacement.

We have shown for the first time that FcγRIIb can be obtained in an active form from E. coli. This is the basis for crystallographic investigations that will soon, due to the already gained crystals of exceptional quality, result in the structure solution of this important molecule. The structure will provide information on the IgG binding site and provide a starting point for the knowledge based design of drugs that interfere with recognition of the ligand by its receptor. Furthermore, because of the high homology between FcγRIIb and other FcRs including FcεRIa it seems possible that these molecules can be produced in the same way, which would provide valuable material for the ongoing research.

1.9 Methods

Protein Chemistry

Recombinant soluble human FcγRIIb was expressed in E. coli, refolded purified and crystallized as described elsewhere (Sondermann et al, 1998B). Briefly, the putative extracellular region of hFcγRIIb2 (Engelhardt et al, 1990) was overexpressed in E. coli. Inclusion bodies were purified by lysozyme treatment of the cells and subsequent sonification. The resulting suspension was centrifuged (30 min 30,000×g) and washed with buffer containing 0.5% LDAO. A centrifugation step and resuspension in LDAO containing buffer was repeated once before this procedure was repeated twice without LDAO. The inclusion bodies were solved in 6 M guanidine hydrochloride and the protein was renaturated as described. The dialyzed and filtrated protein solution was applied to a hIgG sepharose column and eluted by pH jump. The concentrated neutralized fractions were subjected to size-exclusion chromatography on a Superdex-75 column (26/60, Pharmacia).

Crystallization

Crystallization was performed in sitting drops at 20° C. using the vapor diffusion technique. Crystallization screens were performed by changing pH, salt, precipitant and additives. The final crystals used for data collection were grown in 33% PEG2000, 0.2 M sodium acetate, pH 5.4 (orthorhombic form) 26% PEG8000, 0.2 M sodium acetate, pH 5.6, 10% (v/v) 1,4-dioxane, 100 mM sodium chloride (tetragonal form), and 26% PEG8000, 0.2 M sodium acetate, pH 5.6, 5 mM ZN(OAc)$_2$, 100 mM sodium chloride (hexagonal form). The insect cell derived protein was crystallized in 32% PEG6000, 0.2 M sodium acetate, pH 5.3.

Preparation of Heavy-Atom Derivatives

The heavy-atom derivatives were prepared by soaking the crystals in the crystallization buffer containing 2 mM platinum(II)-(2,2'-6,2"terpyridinium) chloride for 24 hours or 10 mM uranylchloride for 8 days.

X-Ray Data Collection

Diffraction data was collected on an image plate system (MAR research) using graphite monochromated CuK$_\alpha$ radiation from a RU200b rotating anode generator (Rigaku) operated at 50 kV and 100 mA. The reflections were integrated with the program MOSFLM 5.50 (Leslie, 1997) and subsequently the data was scaled and truncated to obtain the structure-factor amplitudes using routines from the CCP4 program suite (Collaborative Computational Project, 1994).

Structure Determination

The structure was solved with the standard procedures of the MIR method. From the large number of soaks carried out with different heavy-atom components only the two compounds yielded interpretable Patterson maps. The heavy-atom positions for each derivative were determined from difference Patterson maps and initial phases were calculated. Cross-phased difference Fourier maps were used to confirm heavy atom positions and establish a common origin for the derivatives. Anomalous data were included to discriminate between the enantiomers. The heavy atom parameters were further refined with the program MLPHARE from the CCP4 package leading to the statistics compiled in Table 2. An electron-density map was calculated to a resolution of 2.1 Å and the phases were improved further by solvent flattening and histogram matching with the program DM from the CCP4 suite. The resulting electron density map was of sufficient quality to build most of the amino acid residues. Model building was performed with O (Jones et al, 1991) on an Indigo2 work station (Silicon Graphics Incorporation). The structure refinement was done with XPLOR (Brünger et al, 1987) by gradually increasing the resolution to 1.7 Å using the parameter set of Engh and Huber (Engh & Huber, 1991). When the structure was complete after several rounds of model building and individual restraint B-factors refinement ($R_{fac}$=29%/$R_{Free}$=36%), 150 water molecules were built into the electron density when a Fo-Fc map contoured at 3.5 σ coincided with well defined electron density of a 2Fo-Fc map contoured at 1 σ. The resulting refinement statistic is shown in Table 3.

1.10 Structure Determination

The crystal structure of recombinant soluble human FcγRIIb was solved by multiple isomorphous replacement (MIR) to 1.7 Å resolution, since a structure solution by molecular replacement with isolated domains of the Fc fragment from human IgG1 (Huber et al, 1976, PDB entry 1fc1; Deisenhofer, 1981) failed. The putative extracellular part of the receptor (amino acid residues 1–187 as depicted in SEQ ID NO:2) was used for crystallization trials (Sondermann et al, 1998B) while the model contains the residues 5–176 as the termini are flexible and not traceable into the electron density. Additionally, the model contains 150 water molecules and the refinement statistics are summarized in Table 2. The structure contains a cis proline at position 11. None of the main chain torsion angles is located in disallowed regions of the Ramachandran plot. The fully refined model was used to solve the structure of the same protein in crystals of space group P4$_2$2$_1$2 and of the glycosylated form derived from insect cells in crystals of space group P3$_1$21 (Table 2).

The polypeptide chain of FcγRIIb folds into two Ig-like domains as expected from its affiliation with the immunoglobulin super family. Each domain consists of two beta sheets that are arranged in a sandwich with the conserved disulfide bridge connecting strands B and F on the opposing sheets (FIG. 3). Three anti-parallel β-strands (A1, B, E)

oppose a sheet of 5 β-strands (C', C, F, G, A2), whereby strand A1 leaves the 3-stranded β-sheet and crosses over to the 4-stranded anti-parallel sheet adding the short parallel 5th strand A2. The arrangement of secondary structure elements as well as their connectivity is identical in both domains of the FcγRIIb and a rigid body fit of one domain onto the other revealed a r.m.s. distance of 1.29 Å of 67 matching Cα atoms.

The domains are arranged nearly perpendicularly to each other enclosing an angle of 70 degrees between their long axes forming a heart-shaped overall structure. This arrangement results in an extensive contact region between the domains (FIG. 4). Residues from strand A2 and from the segment linking A2 and A1 of the N-terminal domain intermesh with residues of strands A1 and B from the C-terminal domain. This region is tightly packed and the interaction is strengthened by several hydrogen bonds resulting in a rigid arrangement. This is confirmed by the conservation of the structure in three different space groups. In orthorhombic, tetragonal and hexagonal (insect cell derived) crystal forms a deviation of less than 2° in the interdomain angle is found.

1.11 Overall Structures

The structure of recombinant human FcγRIIb derived from *E. coli* was solved by MIR to 1.7 Å resolution from orthorhombic crystals. An essentially identical structure is found in tetragonal and with protein derived from insect cells in hexagonal crystals. In all three structures the last nine residues of the polypeptide chain were found disordered. The flexibility of the C-terminal linker region between the structured core of the molecule and the transmembrane part may be functionally relevant to allow some reorientation of the receptor to enhance the recognition of the Fc parts in immunocomplexes.

1.12 Homologue Receptors

The Ig domains found in the Ig super family of proteins are characterized by a beta sandwich structure with a conserved disulfide bridge connecting two strands of the opposing sheets. The typical arrangement of 3 and 4 anti parallel beta strands that form a sandwich as found in FcγRIIb occurs also in the T cell receptor, Fc fragment, CD4 or the Fab fragment. A structural alignment of the individual Ig domains of these molecules with the two domains of FcγRIIb shows a common, closely related structure. The relative arrangement of the domains, however, is not related in these molecules and covers a broad sector. Despite the structural similarity between Ig domains from different molecules and the strikingly low r.m.s. deviation of Cα atoms that result when the two domains of FcγRII are superimposed, no significant sequence similarity is found (FIGS. 5a and 5b). A structure-based sequence alignment shows a conserved hydrophobicity pattern along the sequence of the domains, together with, beside the cysteins, only few identical amino acid residues. We first prepared a structure-based alignment of the two C-terminal domains of the IgG1 heavy chain and the FcγRIIb and added the sequences of the other related FcγR and the FcεRIa domains. This shows that the sequences of the three domain FcγRI and the two domain receptors are compatible with the hydrophobicity pattern of Ig domains and several conserved amino acid residues are revealed. Firstly, the different domains of an FcR are more related to each other than to Ig domains from other molecules of the Ig super family. Secondly, the N-terminal domains of the receptors relate to each other as the second domains do. Thirdly, the sequence of the third domain of FcγRI shows features from both groups of domains. Taken together, we confirm the affiliation of the FcRs to the Ig super family and speculate that all FcR-domains originate from a common ancestor, an ancient one domain receptor that acquired a second domain by gene duplication. Further divergent development of such a two domain receptor resulted in the present diversity, including FcγRI that acquired a third domain.

Conservation of these amino acid residues that contribute to the interdomain contact in FcγRIIb in the alignment are a hint to a similar domain arrangement in different receptors. In Table 4 the residues contributing with their side chains to the interdomain contact (FIG. 4) are compiled for FcγRIIb together with the corresponding amino acid residues in other receptors according to the structure-based sequence alignment of FIG. 5b. Except for Asn15, which is not conserved between the FcRs, the involved residues are identical or conservatively replaced providing strong support for a similar structure and domain arrangement in all FcRs.

1.13 The Contact Interface to IgG

Limited information about the interactions of FcRs with their ligands is available from mutagenesis studies (Hogarth et al, 1992; Hulett et al, 1994; Hulett et al, 1995). By systematically exchanging loops between the β-strands of FcγRIIa for FcεRIa amino acid residues the B/C, C'/E and F/G loops of the C-terminal domain were evaluated as important for ligand binding (FIG. 3, FIG. 5b). In the structure model these loops are adjacent and freely accessible to the potential ligand. Additionally, most of the amino acid residues in these loops were exchanged for alanines by single site mutations which resulted in a drastic alteration of the affinity of FcγRIIa to dimeric human IgG1. Also, the single amino acid exchange Arg 131 to His in the C-terminal domain (C'/E loop) in the high responder/low responder polymorphism, which alters the affinity of the FcγRIIa to murine IgG1, points to that region. Thus, the amino acid residues in this area are either important for ligand binding or the structural integrity of that region. Here, the structure shows a clustering of the hydrophobic amino acid residues Pro 114, Leu 115 and Val 116 in the neighbourhood of Tyr 157. This patch is separated from the region Leu 159, Phe 121 and Phe 129 by the positively charged amino acid residues Arg 131 and Lys 117 which protrude from the core structure (FIG. 5b).

1.14 Glycosylation

In the sequence of FcγRIIb three potential N-glycosylation sites are found. All three sites are on the surface of the molecule and are accessible. They are located in the E/F loops (N61 and N142) of both domains and on strand E (N135) of the C-terminal domain (FIG. 3, FIG. 6). Since the material used for the solution of this structure was obtained from *E. coli*, it does not contain carbohydrates, while the FcRs isolated from mammalian cells are highly glycosylated. The three potential glycosylation sites are located rather far from the putative IgG binding region, and non-glycosylated FcγRIIb binds human IgG, suggesting a minor role of glycosylation in binding. This was confirmed by the structure of the FcγRIIb produced in insect cells which is glycosylated (Sondermann et al, 1998A). Except for a 2° change of the interdomain angle possibly due to different crystal contacts, no differences between the glycosylated and unglycosylated protein structures were found. The three glycosylation sites are only optionally used as shown by SDS-PAGE where the material appears in 4 bands. No additional electron density for those sugars was found a consequence of chemical and structural heterogeneity.

EXAMPLE 2 shFcγRIIa (Soluble Human FcγRIIa)

The procedures were performed according to example 1 except for the indicated changes:

2.1 Cloning and Expression shFcγRIIa was generated by mutating the respective wild-type cDNA (Stengelin et al., 1988) and expressed according to example 1 with the mutagenous primers listed in table 5. For the expression of the protein a pET22b+ vector was chosen.

2.2 Refolding and Purification shFcγRIIa was refolded according to example 1 with the respective refolding buffer listed in table 6.

2.3 Crystallisation shFcγRIIa was crystallised as described under conditions indicated in table 7.

2.4 Structure Determination

The structure was solved with the method of isomorphous replacement with shFcγRIIb as search model.

EXAMPLE 3 shFcγRIII (Soluble Human FcγRIII)

The procedure was performed according to example 1 except for the indicated changes:

3.1 Cloning and Expression shFcγRIII was generated by mutating the respective wild-type cDNA (Simmons & Seed, 1988) and expressed according to example 1 with the mutagenous primers listed in table 5. For the expression of the protein a pET22b+ vector was chosen.

3.2 Refolding and Purification shFcγRIII was refolded according to example 1 with the respective refolding buffer listed in table 6.

3.3 Crystallisation shFcγRIII was crystallised as described under conditions indicated in table 7.

3.4 Structure Determination

The structure was solved with the method of isomorphous replacement with shFcγRIIb as search model.

3.5 Crystallisation of a shFcγRIII:hFc1 Complex hIgG1 derived from the serum of a myeloma patient was used to prepare Fc-fragments (hFc1) by digestion with plasmin (Deisenhofer et al., 1976). The resulting Fc-fragments were separated from the Fab-fragments by protein A chromatography. Partially digested hIgG was removed by size exclusion chromatography with MBS (2 mM MOPS, 150 mM NaCl, 0.02% sodium azide, pH 7.0) as running buffer. Equimolar amounts of hFc1 and shFcgRIII were mixed and diluted with MBS to a concentration of 10 mg/ml. The complex was crystallised as described under conditions indicated in table 5.

EXAMPLE 4 shFcεRII (Soluble Human FcεRII)

The procedure was performed according to example 1 except for the indicated changes:

4.1 Cloning and Expression

FcεRII was generated by mutating the respective wild-type cDNA (Kikutani et al., 1986) and expressed according to example 2 with the mutagenous primers listed in table 5. For the expression of the protein a pET23a+ vector was chosen.

4.2 Refolding and Purification

Refolding of shFcεRII was achieved as described in example 1, with the exception that prior to rapid dilution the dissolved inclusion bodies were dialysed against 6M guanidine chloride, 20 mM sodium acetate, pH 4.0. shFcεRII was refolded according to example 1 with the respective refolding buffer listed in table 6. After refolding the protein solution was dialysed against PBS, concentrated 100-fold and purified by gel filtration chromatography on Superdex 75. This yielded pure shFcεRII which was dialysed against 2 mM TRIS/HCl, 150 mM NaCl, 0.02% sodium azide, pH 8.0, concentrated to 10 mg/ml and stored at 4° C.

EXAMPLE 5 shFcγRI (Soluble Human FcγRI)

The procedure was performed according to example 1 except for the indicated changes:

5.1 Cloning and Expression shFcγRI was generated by mutating the respective wild-type cDNA (Allen & Seed, 1988) and expressed according to example 1 with the mutagenous primers listed in table 5. For the expression of the protein a pET32a+ vector was chosen, which contains after the N-terminal thioredoxin a hexahistidine-tag with a C-terminal thrombin cleavage site followed by the shFcγRI in frame with the mentioned proteins and amino acid residues. For the overexpression of the fusion protein the E. coli strain BL21(DE3) containing the plasmids pUBS and pLysS (Novagen) was used.

The purified inclusion bodies were solubilised in 6M guanidine-HCl, 10 mM β-mercaptoethanol, 50 mM Tris pH8.0 and bound to a Ni-NTA column (Qiagen). The elution was performed with an imidazole gradient ranging from 0 to 1M imidazole. The eluted protein was dialysed against a 1000 fold volume of 150 mM NaCl, 50 mM Tris pH8.0, 2 mM GSH, 0.5 mM GSSG for 24 hours at 4° C. After concentrating the protein solution to 25% of the initial volume, thrombin was added. After 6 h of incubation at 37° C. the N-terminal thioredoxin and the His-tag were removed completely as verified by N-terminal sequencing. During this digestion the shFcgRI precipitated quantitatively out of solution.

5.2 Refolding and Purification shFcγRI was refolded according to example 1 with the respective refolding buffer listed in table 6. After the redox potential decresased to 1 mM the solution was dialysed against PBS pH 8.0 and concentrated.

The refolded Protein was analysed by size exclusion chromatography, which yielded a peak of the proposed monomeric receptor and non reducing SDS-PAGE which showed a major band at 30 kDa.

EXAMPLE 6 shFcεRIa (Soluble Human FcεRIa)

The procedure was performed according to example 1 except for the indicated changes:

6.1 Cloning and Expression shFcεRI was generated by mutating the respective wild-type cDNA (Kochan et al., 1988) and expressed according to example 1 with the mutagenous primers listed in table 5. For the expression of the protein a pET23a+ vector was chosen.

Lane 1: Molecular weight marker. Lane 2: *E. coli* lysate before induction. Lane 3: *E. coli* lysate 1 h after induction. Lane 4: *E. coli* lysate 4 h after induction. Lane 5: Purified inclusion bodies of sFcγRIIb. Lane 6: Eluate of the hIgG affinity column. Lane 7: Pooled fractions of the gel filtration column.

Figure 1:
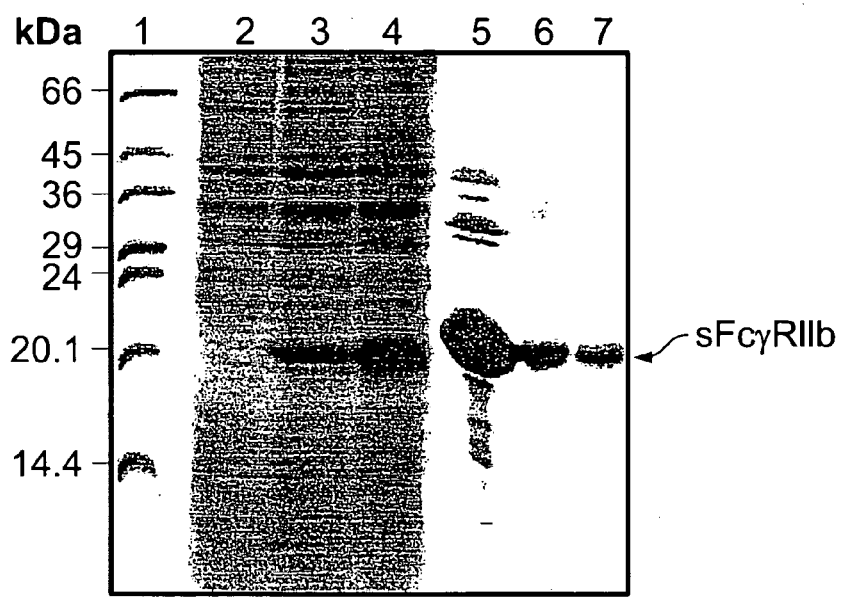
FIG. 1: 15% reducing SDS PAGE showing the purification of sFcγRIIb
Figure 2:
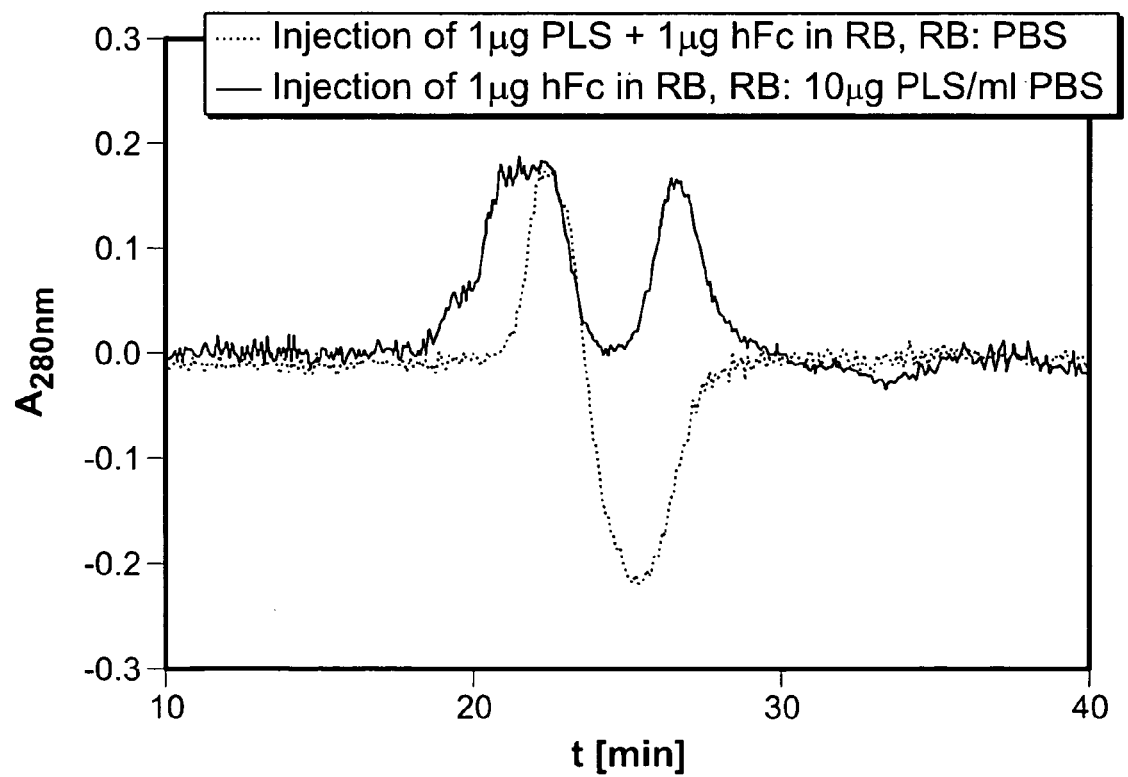

FIG. 2: Equilibrium gel filtration

1 µg hFc solved in 10 µl equilibration buffer (10 µg sFcγRIIb/ml PBS) was applied to a size exclusion chromatography column and the absorbance of the effluent was measured (280 nm) as a function of time. The injected Fc fragment forms a complex with the sFcγRIIb in the equilibration buffer (t=22 min). The negative peak of consumed sFcγRIIb is observed at t=26 min.

Figure 3:
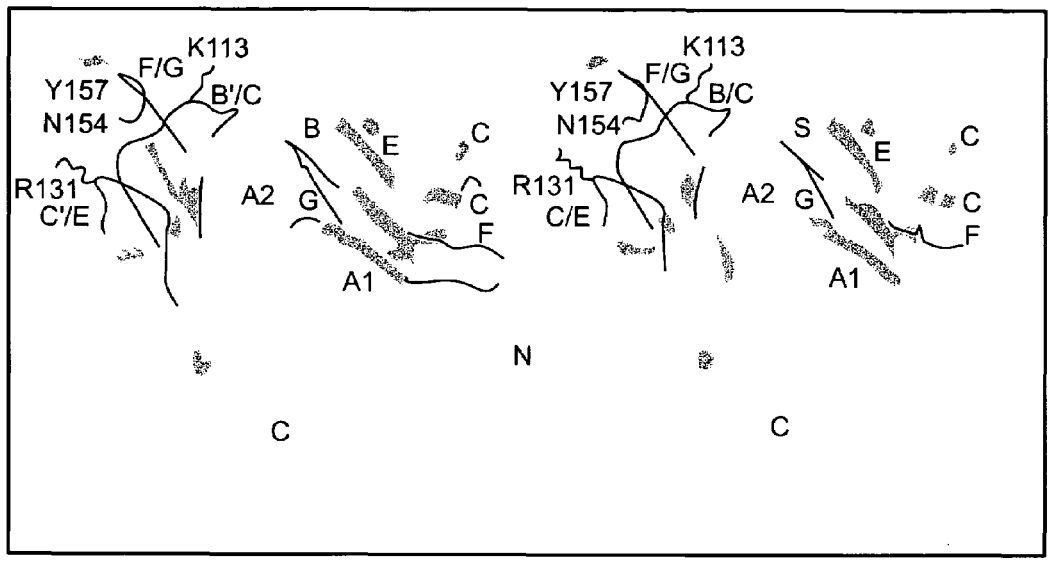

FIG. 3: Overall structure of human sFcγRIIb

Stereo ribbon representation of the sFcγRIIb structure. The loops supposed to be important for IgG binding are depicted in red with some of the residues within the binding site and the conserved disulfide bridge in ball and stick representation. The potential N-glycosylation sites are shown as green balls. The termini are labeled and the β-strands are numbered consecutively for the N-terminal domain in black and for the C-terminal domain in blue. The figure was created using the programs MOLSCRIPT (Kraulis, 1991) and RENDER (Merritt and Murphy, 1994).

Figure 4:
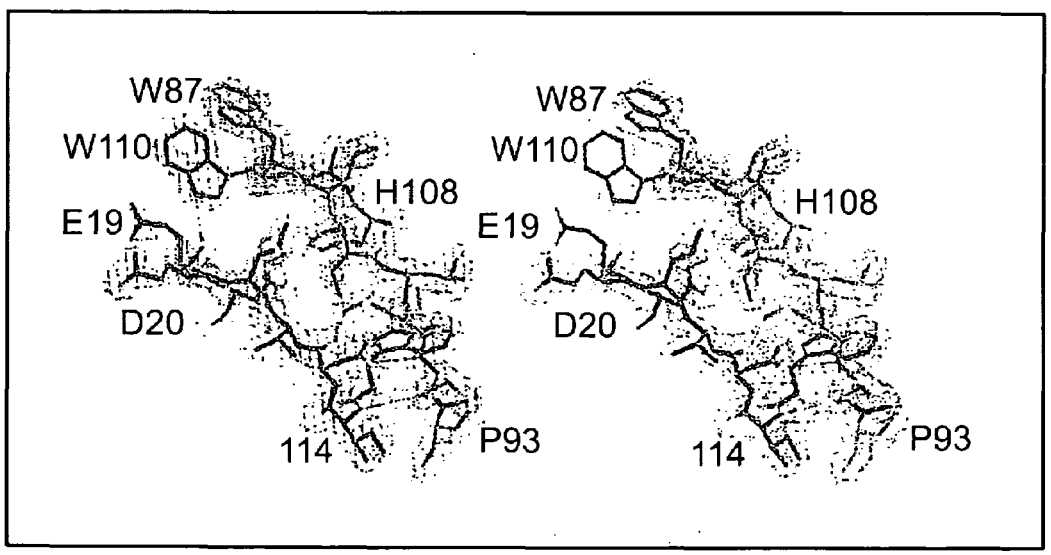

FIG. 4: Interdomain contacts

The figure shows a close-up on the residues involved in the interdomain contacts of sFcγRIIb. The amino acid residues of the N-terminal domain are depicted blue and the residues of the C-terminal domain yellow. The model is covered by a 2Fo-Fc electron density contoured at 1 σ obtained from the final coordinates. Hydrogen bridges between the domains are represented by white lines. The figure was created using the program MAIN (Turk, 1992).

FIG. 5a: Superposition of the two FcγRIIb domains and the CH2 domain of human IgG1

Both domains of FcγRIIb and the CH2 domain of hIgG1 were superimposed. The N-terminal domain is depicted in blue, the C-terminal domain in red and the CH2 domain of hIgG1 in green. The respective termini are labeled and the conserved disulfide bridges are depicted as thin lines.

Figure 5B:
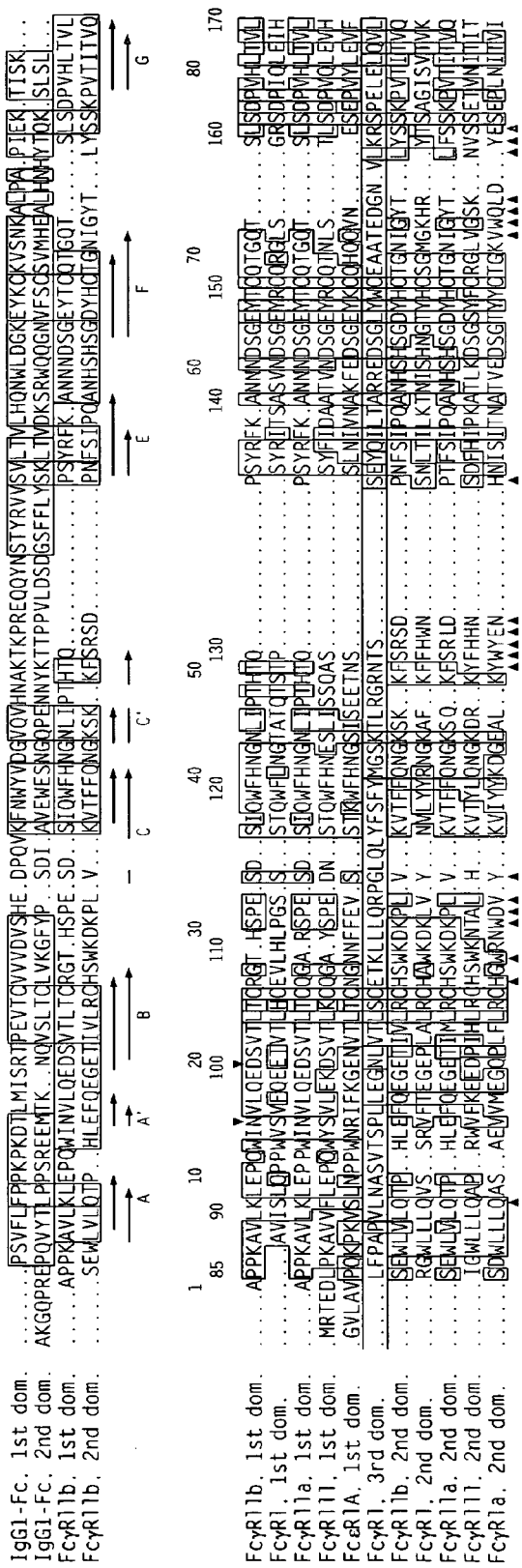

FIG. 5b: Structure based sequence alignment of the sFcγFIIb domains with domains of other members of the FcR family The upper part of the figure shows the structure based sequence alignment of the FcγRIIb and hIgG1 Fc fragment domains performed with the program GBF-3D-FIT (Lessel & Schomburg, 1994). Amino acid residues with a Cα distance of less than 2.0 Å in the superimposed domains are masked: lilac for matching residues between the Fc fragment domains; yellow for residues in the FcγRIIb domains; and green when they can be superimposed in all four domains. The β-strands are indicated below this part of the alignment and are labeled consistent with FIG. 3.

The lower part of the figure shows the alignment of the amino acid sequences from the other FcγRs and the homologue FcεRIa to the profile given in the upper part of the figure using routines from the GCG package (Genetics Computer Group, 1994). The upper and lower row of numbering refer to the N- and C-terminal domains of FcγRIIb. The conserved cysteins are typed in magenta and the potential glycosylation sites in blue. Identical residues within the first domain are masked orange, those in the second domain pink and green when the residues are conserved within both domains. The less conserved third domain of FcγRI is aligned between the first and the second domains. Red arrows point to residues that are involved in side chain contacts between the first and the second domain while blue arrows depict residues that are relevant for IgG binding. The figure was produced with the program ALSCRIPT (Barton, 1993).

FIG. 6: The putative binding sites of FcγRIIb

Solid surface representations of FcγRIIb as produced with GRASP (Nicholls et al, 1991), the color coding is according to the relative surface potential from negative (red) to positive (blue). FIG. 6a shows the molecule as in FIG. 3 by a rotation of about 90° counter-clockwise around the vertical. In FIG. 6b the molecule is rotated 90° clockwise around the same axis. Both views show the putative binding regions on the C-terminal (FIG. 6a) and the N-terminal domain (FIG. 6b). The amino acid residues discussed in the text are labeled.

Figure 7:
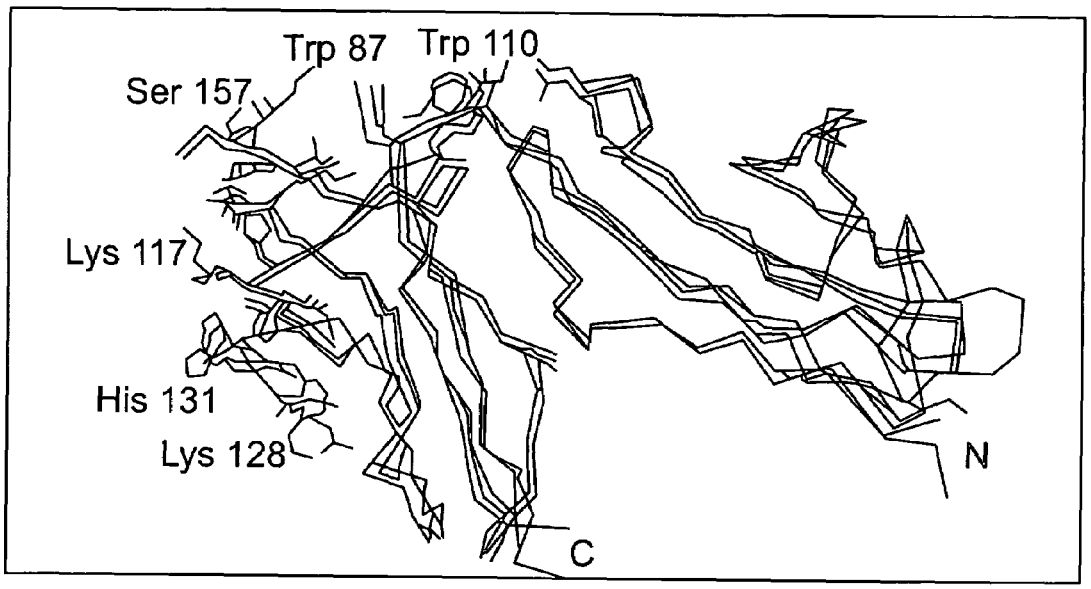

FIG. 7: Cα-trace of the superpositioned structures of the Fcγ-receptors

FcγRIII red, FcγRIIa green and FcγRIIb blue. Residues important for IgG binding are shown in ball-and-stick. The N- and C-termini are labelled.

Figure 8:
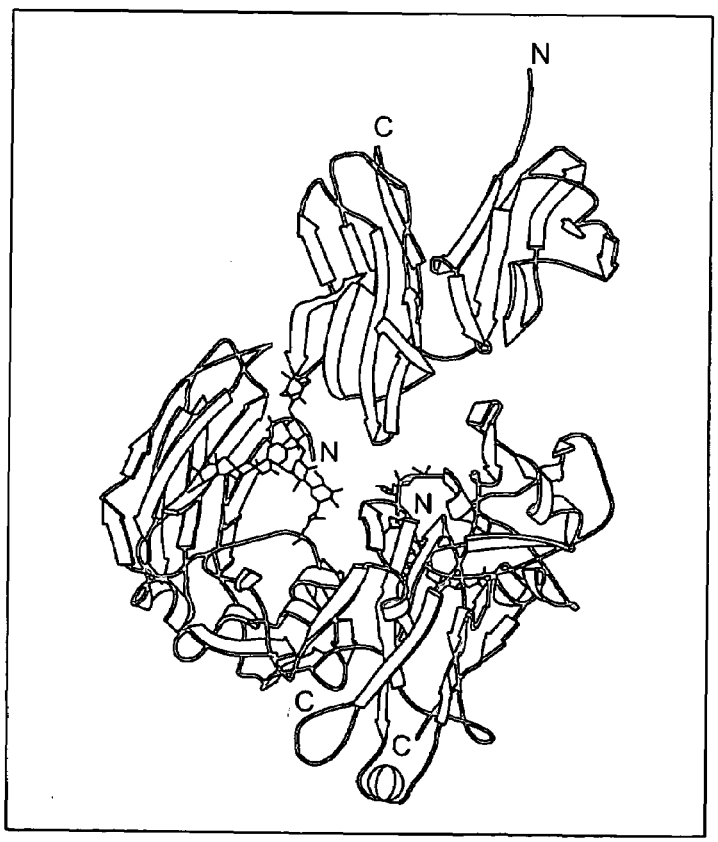

FIG. 8: Overview of the FcγRIII/Fc-fragment crystal structure in ribbon representation The sugar residues bound to the Fc-Fragment are indicated in ball-and-stick. The FcγRIII (blue) binds in the lower hinge region between chain-B (red) and chain-A (green) of the Fc-fragment.

Figure 9:
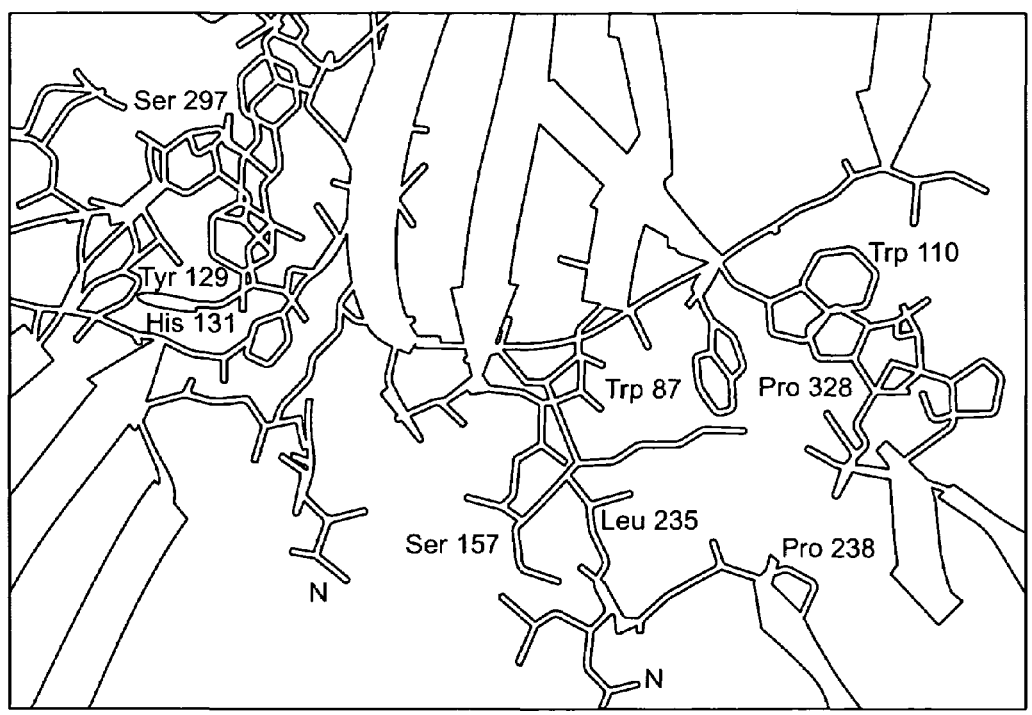

FIG. 9: Close-up on the binding region of the FcγRIII and the Fc-fragment

The colour scheme is in agreement to FIG. 8 and residues important for complex formation are shown in ball-and-stick.

Figure 10A:
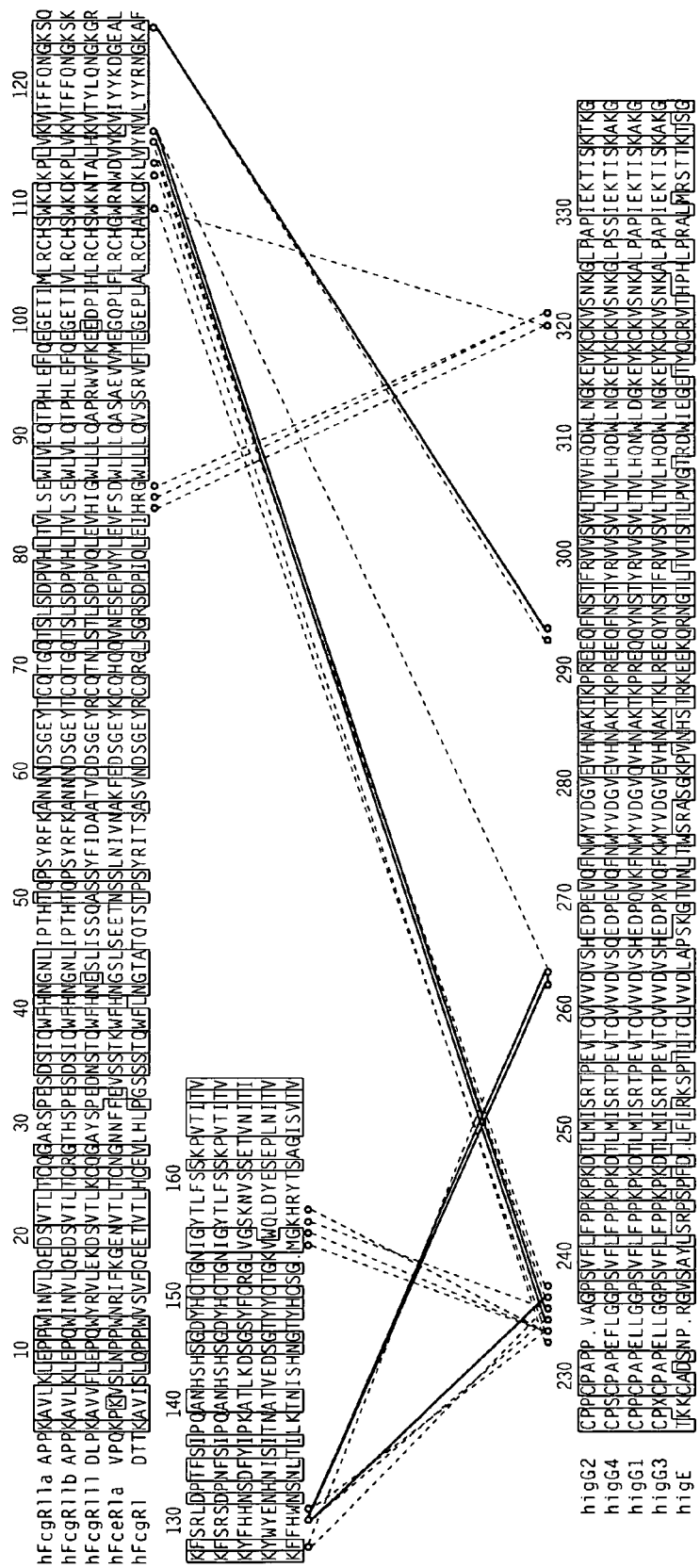

FIG. 10a:

In the upper part of FIG. 10a a structure based sequence alignment of the Fc-Receptor ecto-domains is shown. Conserved residues are shaded yellow and identical residues orange. The lower part of the figure shows a part of the alignment of human antibody sequences. Residues of the human FcγRIII in contact with the Fc-fragment in the complex crystal structure are connected by lines (black for hydrophobic interaction, red for salt bridges and blue for hydrogenbridges). Residues from the Fc-receptor in contact with the A-chain of the Fc-fragment are connected with dashed lines and those in contact with the B-chain of the Fc-fragment with solid lines. Red, blue and black lines represent charged, polar and other contacts, respectively.

Figure 10B:
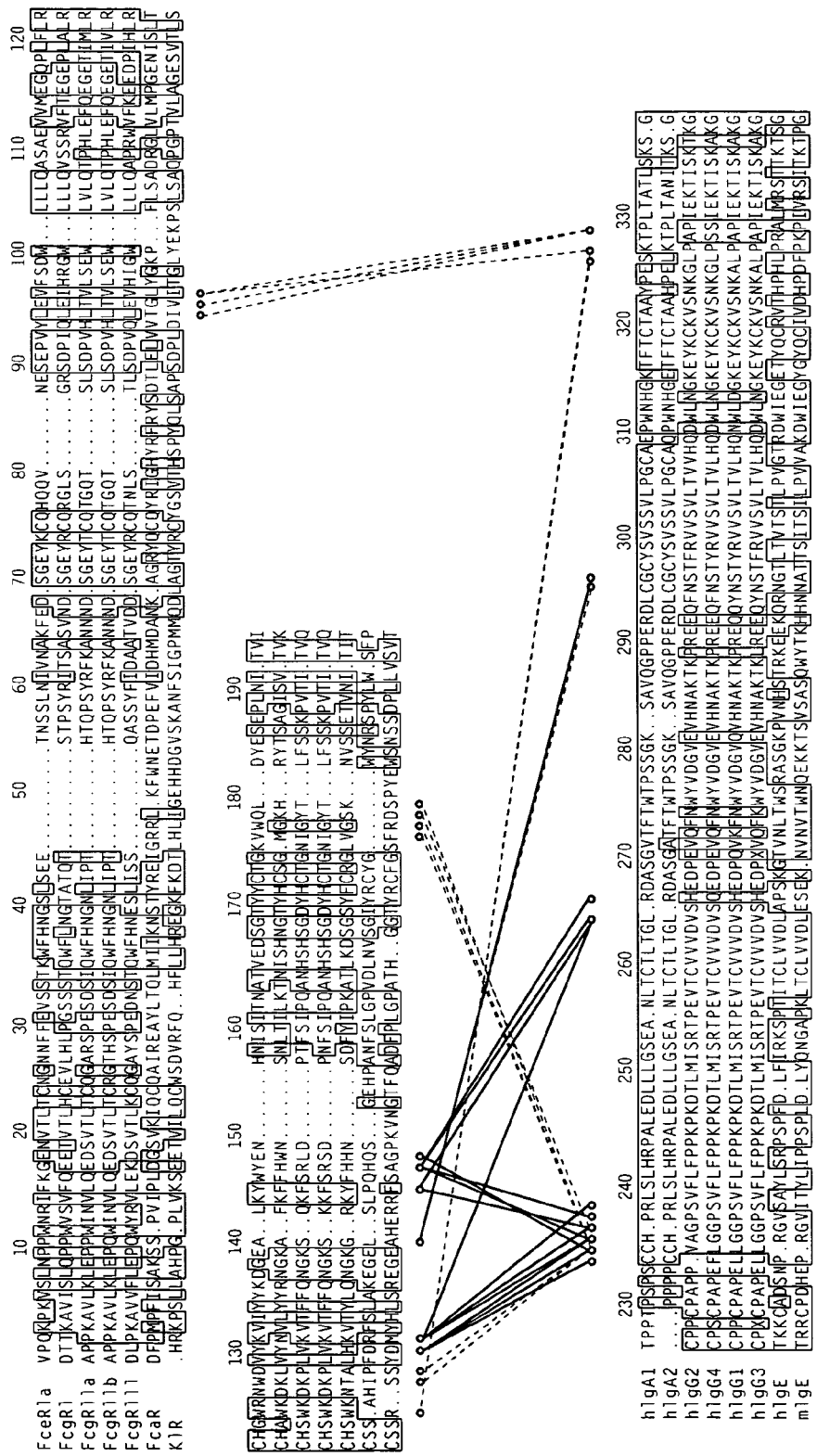

FIG. 10b:

In the upper part of FIG. 10b a structure based sequence alignment of the Fc-Receptor ecto-domains is shown. Conserved residues are shaded yellow and identical residues orange. Conserved residues within the less related Kir and FcA-Receptor sequences are shaded blue. The lower part of the figure shows a part of the alignment of human antibodies with the mouse IgE (mIgE) sequence. Residues of the human FcγRIII in contact with the Fc-fragment in the complex crystal structure are connected by lines (black for hydrophobic interaction, red for salt bridges and blue for hydrogen bonds). Residues from the Fc-receptor in contact with the A-chain of the Fc-fragment are connected with dashed lines and those in contact with the B-chain of the Fc-fragment with solid lines. Red, blue and black lines represent charged, polar and other contacts, respectively.

FIG. 11 and FIG. 12:

FIG. 11 and FIG. 12 show an alignment of the produced sFcγR, sFcεRIa and the short form of sFcεRII and the produced sFcγR and sFcεRIa without sFcεRII, respectively.

TABLE 1

Crystallographic results
The obtained preliminary crystallographic data are shown in this table.

|  | Orthorhombic | Tetragonal | Hexagonal |
|---|---|---|---|
| Space group | $P2_12_12_1$ [19] | $P4_22_12$ [94] | P3 [143] |
| Unit cell dimensions | a = 40.8 Å, b = 50.9 Å, c = 80.5 Å, α = 90°, β = 90°, γ = 90° | a = 85.7 Å, b = 85.7 Å, c = 63.4 Å, α = 90°, β = 90°, γ = 90° | a = 80.9 Å, b = 80.9 Å, c = 157.0 Å, α = 90°, β = 90°, γ = 90° |
| $R_{merge}$ | 5.8% | 9.8% | 13.6% |
| Resolution | 1.7 Å | 2.7 Å | 3.8 Å |
| Unique | 18,040 | 6,616 | 7,210 |
| Completeness | 89.1% | 97.1% | 63.0% |
| Multiplicity | 3.5 | 4.4 | 1.3 |
| $V_M$, molecules per asymmetric unit, solvent content | 2.09 Å³/Da, 1 mol., 41% solvent | 2.91 Å/Da, 1 mol, 58% solvent | 2.97 Å/Da, 5 mol, 59% solvent |

TABLE 2

Data collection statistics

| Derivative | Space Group | No. of unique reflections | Multiplicity | Resolution (Å) | Completeness (overall/last shell) (%/%) | $R_m$ (%) | No. of sites | Phasing power |
|---|---|---|---|---|---|---|---|---|
| NATI | $P2_12_12_1$ | 18009 | 3.6 | 1.74 | 92.9/86.4 | 5.5 | | |
| NATI | $P4_22_12$ | 6615 | 4.5 | 2.70 | 97.1/94.3 | 10.1 | | |
| NATI-Baculo | $P3_121$ | 3545 | 2.5 | 3.0 | 93.0/98.9 | 14.4 | | |
| UOAc | $P2_12_12_1$ | 7722 | 4.2 | 2.1 | 96.8/95.7 | 7.3 | 1 | 1.79 |
| $PtP_Y$ | $P2_12_12_1$ | 5520 | 3.9 | 2.3 | 89.7/49.6 | 10.5 | 1 | 1.39 |

TABLE 3

Refinement statistics

| | |
|---|---|
| Resolution range (Å) | 8.0–1.74 Å |
| No. of unique reflections (F > 0 σ (F)) | 16252 |
| R factor | 19.4 |
| $R_{free}$* | 27.9 |
| No. of atoms per asymmetric unit | |
| protein | 1371 |
| solvent | 150 |
| Rms deviation from ideal geometry | |
| bond length (Å) | 0.009 |
| bond angle (°) | 2.007 |
| Average B factors (Å²) | |
| protein main chain | 18.8 |
| protein side chain | 25.2 |
| solvent | 36.7 |
| Rms deviation of bonded B factors (Å²) | 4.1 |

*$R_{free}$: 5% of the reflections were used as a reference data set and were not included in the refinement.

TABLE 4

Residues that contribute to the interdomain contact via side chains

| FcγRIIb | FcγRIIa | FcγRIII | FcγRI | FcεRIa |
|---|---|---|---|---|
| Asn15 | Asn | Ser | Ser | Arg |
| Asp20 | Asp | Asp | Glu | Glu |
| Gln91 | Gln | Gln | Gln | Gln |
| His108 | His | His | His | His |
| Trp110 | Trp | Trp | Trp | Trp |

TABLE 5

Primers used for the amplification of the FcRs

| Construct | 5'-Primer | 3'-Primer |
|---|---|---|
| sFcγRI | 5'-CACCC*CATATG*GCAGTGATCTCTTT-3' | 5'-AGGA*CTCGAGA*CTAGACAGGAGTTGGTAAC-3' |
| sFcγRIIa | 5'-ACAGTC*ATATG*GCAGCTCCCC-3' | 5'-AAAAAAA*GCTTCA*GGGCACTTGGAC-3' |
| sFcγRIIb | 5'-AATTCC*ATGG*GGGACACCTGCAGCTCCC-3' | 5'-CCCAGT*GTCGAC*AGC*CTA*AATGATCCCC-3' |
| sFcγRIII | 5'-AAAAAAACAT*ATG*CGGACTGAAG-3' | 5'-AAAAAAGC*TTA*ACCTTGAGTGATG-3' |
| sFcεRIa | 5'-GATGGCC*ATATG*GCAGTCCCTCAG-3' | 5'-CAAT*GGATC*CTAAAATTGTAGCCAG-3' |
| sFcεRII | 5'-AAAAAAACAT*ATG*GAGTTGCAGG-3' | 5'-TGGCT*GGATCC*ATGC*TCA*AG-3' | introduced restriction sites are underlined, start- and stop-codons are depicted as bold-italics.

TABLE 6

Refolding Conditions for the FcRs

| Construct | Buffer |
|---|---|
| sFcγRI | 0.1 M TRIS/HCl, 1.2 M arginine, 150 mM NaCl, 5 mM GSH, 0.5 mM GSSG, 0.02% sodium azide, pH 8.0 |
| sFcγRIIa | 0.1 M TRIS/HCl, 1.4 M arginine, 150 mM NaCl, 2 mM GSH, 0.5 mM GSSG, 0.02% sodium azide, pH 8.0 |
| sFcγRIIb | 0.1 M TRIS/HCl, 1.4 M arginine, 150 mM NaCl, 5 mM GSH, 0.5 mM GSSG, 0.02% sodium azide, pH 8.0 |
| sFcγRIII | 0.1 M TRIS/HCl, 1.0 M arginine, 150 mM NaCl, 2 mM GSH, 0.5 mM GSSG, 0.02% sodium azide, pH 8.0 |
| sFcεRII | 0.1 M TRIS/HCl, 0.8 M arginine, 150 mM NaCl, 5 mM GSH, 0.5 mM GSSG, 0.02% sodium azide, pH 8.3 |

TABLE 7

Crystallisation Conditions for the FcRs

| Construct | Condition | Space group, cell constants | Resolution |
|---|---|---|---|
| sFcγRIIa | 26% PEG 8000, 0.2 M sodium acetate/acetic acid pH 4.6, 0.02% sodium azide | C2, a = 80.4 Å, b = 49.7 Å, c = 54.6 Å, a = g = 90°, b = 128.1° | 3.0 Å |
| sFcγRIIb | 33% PEG 2000, 0.2 M sodium acetate, 0.02% sodium azide, pH 5.4 | P212121, a = 40.8 Å, b = 50.9 Å, c = 80.5 Å, a = b = g = 90° | 1.7 Å |
| sFcγRIII | 22% PEG 8000, 0.1 M MES/TRIS pH 7.8, 0.02% sodium azide | P22121, a = 36.7 Å, b = 60.3 Å, c = 85.6 Å, a = b = g = 90° | 2.5 Å |
| sFcγRIII: hFcl | 6% PEG 8000, 0.1 M MES/TRIS pH 5.6, 0.2 M Na/K tartrate, 0.02% sodium azide | P6522, a = b = 115.0 Å, c = 303.3 Å, a = b = 90°, g = 120° | 3.3 Å |
| sFcγRIII | 22% PEG 8000, 0.1 M MES/TRIS pH 7.8, 0.02% sodium azide | P22121, a = 36.7 Å, b = 60.3 Å, c = 85.6 Å, a = b = g = 90° | 2.5 Å |

REFERENCES

Ades, E. W., Phillips, D. J., Shore, S. L., Gordon, D. S., LaVia, M. F., Black, C. M., Reimer, C. B. (1976), Analysis of mononuclear cell surfaces with fluoresceinated Staphylococcal protein A complexed with IgG antibody or heat-aggregated γ-globulin, J. Immunol. 117, 2119.

Allen J. M., Seed B.; "Nucleotide sequence of three cDNAs for the human high affinity Fc receptor (FcRI)"; Nucleic Acids Res. 16:11824–11824(1988).

Amigorena, S., Bonnerot, C., Drake, J. R., Choquet, D., Hunziker, W., Guillet, J. G., Webster, P., Sautes, C., Mellman, I., Fridman, W. H. (1992), Cytoplasmic domain heterogeneity and functions of IgG Fc receptors in B lymphocytes, Science 256, 1808–1812.

Barton, G. C. (1993), ALSCRIPT: tool to format multiple sequence alignments, Prot. Eng. 6, 37–40.

Bazil, V. and Strominger, J. L. (1994), Metalloprotease and serine protease are involved in cleavage of CD43, CD44, and CD16 from stimulated human granulocytes, J. Immunol. 152, 1314–1322.

Brünger, A. T., Kuriyan, J., Karplus, M. (1987), Crystallographic R factor refinement by molecular dynamics, Science 35, 458–460.

Burmeister, W. P., Huber, A. H., Bjorkman, P. J. (1994), Crystal structure of the complex of rat neonatal Fc receptor with Fc, Nature 372, 379–383.

Ceuppens, J. L., Baroja, M. L., van Vaeck, F., Anderson, C. L. (1988), Defect in the membrane expression of high affinity 72 kD Fcγ receptors on phagocytic cells in four healthy subjects, J. Clin. Invest. 82, 571–578.

Collaborative computational project, Number 4 (1994), The CCP4 suite: Programs for protein crystallography, Acta crystallogr. D50, 760–763.

Deisenhofer, J., Jones, T. A., Huber, R., Sjodahl, J., Sjoquist, J. (1978), Crystallization, crystal structure analysis and atomic model of the complex formed by a human Fc fragment and fragment B of protein A from *Staphylococcus aureus*, Z. Phys. Chem. 359, 975–985.

Deisenhofer, J. (1981), Crystallographic refinement and atomic models of a human Fc fragment and its complex with fragment B of protein A from *Staphylococcus aureus* at 2.9- and 2.8A resolution, Biochemistry 20, 2361–2370.

Deisenhofer J., Colman P M., Huber R., Haupt H., Schwick G.; "Crystallographic structural studies of a human Fc-fragment. I. An electron-density map at 4 Å resolution and a partial model"; Hoppe-Seyler's Z. Physiol. Chem. 357: 435–445(1976).

Dulau, L., Cheyrou, A., Aigle, M. (1989), Directed mutagenesis using PCR, Nucleic Acids Res. 17, 2873.

Ellman (1959), Tissue sulfhydryl groups, Arch. Biochem. Biophys. 82, 79–77.

Engelhardt, W., Geerds, C., Frey, J. (1990), Distribution, inducibility and biological function of the cloned and expressed human βFc receptor II, Eur. J. Immunol. 20, 1367–1377.

Engh, R. A. and Huber, R. (1991), Accurate bond and angle parameters for X-ray protein structure refinement, Acta crystallogr. A47, 392–400.

Fleit, H. B., Kobasiuk, C. D., Daly, C., Furie, R., Levy, P. C., Webster, R. O. (1992), A soluble form of FcγRIII is present in human serum and other body fluids and is elevated at sites of inflammation, Blood 79, 2721–2728.

Fridman, W. H., Bonnerot, C., Daeron, M., Amigorena, S., Teillaud, J.-L., Sautès, C. (1992), Structural bases of Fcγ receptor functions, Immunol. Rev. 125, 49–76.

Fridman, W. H., Teillaud, J.-L., Bouchard, C., Teillaud, C., Astier, A., Tartour, E., Galon, J., Mathiot, C., Sautès, C. (1993), Soluble Fcγ receptors, J. Leukocyte Biol. 54, 504–512.

Gabb, H. A., Jackson, R. M., Sternberg, M. J. E. (1997), Modelling protein docking using shape complementarity, electrostatics and biochemical information, J. Mol. Biol. 272, 106–120.

Galon, J., Bouchard, C., Fridman, W. H., Sautès, C. (1995), Ligands and biological activities of soluble Fcγ receptors, Immunol. Lett. 44, 175–181.

Genetics Compouter Group (1994), Program Manual for the Wisconsin Package Version 8, Madison, Wis.

Gordon, J. et al., (1980), The molecules controlling B lymphocytes. Immunol. Today, 8: 339–344.

Grodberg, J. and Dunn, J. J. (1988), OmpT encodes the *Escherichia coli* outer membrane protease that cleaves T7 RNA polymerase during purification, J. Bacteriol. 170, 1245–1253.

Hogarth, P. M., Hulett, M. D., Ierino, F. L., Tate, B., Powell, M. S., Brinkworth, R. I. (1992), Identification of the immunoglobulin binding regions (IBR) of FcγRII and FcεRI, Immunol. Rev. 125, 21–35.

Homsy, J., Meyer, M., Tateno, M., Clarkson, S., Levy, J. A. (1989), The Fc and not CD4 receptor mediates antibody enhancement of HIV infection in human cells, Science 244, 1357–1360.

Hoover, R. G., Lary, C., Page, R., Travis, P., Owens, R., Flick, J., Kornbluth, J., Barlogie, B. (1995), Autoregulatory circuits in myeloma: Tumor cell cytotoxity mediated by soluble CD16, J. Clin. Invest. 95, 241–247.

Huber, R., Deisenhofer, J., Colman, P. M., Matsushima, M. and Palm, W. (1976), Crystallographic structure studies of an IgG molecule and an Fc fragment, Nature 264, 415–420.

Hulett, M. D., Witort, E., Brinkworth, R. I., McKenzie, I. F. C., Hogarth, P. M. (1994), Identification of the IgG binding site of the human low affinity receptor for IgG FcγRII, J. Biol. Chem. 269, 15287–15293.

Hulett, M. D., Witort, E., Brinkworth, R. I., McKenzie, I. F. C., Hogarth, P. M. (1995), Multiple regions of human FcγRII (CD32) contribute to the binding of IgG, J. Biol. Chem. 270, 21188–21194.

Ierino, F. L., Powell, M. S., McKenzie, I. F. C., Hogarth, P. M. (1993), Recombinant soluble human FcγRII: Production, characterization, and inhibition of the arthus reaction, J. Exp. Med. 178, 1617–1628.

Jancarik, J. and Kim, S. H. (1991), Sparse matrix sampling: A screening method for crystallization of proteins, J. Appl. Crystallogr. 24, 409–411.

Jones, T. A., Zou, J.-Y., Cowan, S. W., Kjeldgaard, M. (1991), Improved methods for building protein models in electron density maps and the location of errors in these models, Acta crystallogr. A47, 110–119.

Kikutani H., Inui S., Sato R., Barsumian E. L., Owaki H., Yamasaki K., Kaisho T., Uchibayashi N., Hardy R. R., Hirano T., Tsunasawa S., Sakiyama F., Suemura M., Kishimoto T.; "Molecular structure of human lymphocyte receptor for immunoglobulin E"; Cell 47(5):657–665 (1986).

Khayat, D., Soubrane, C., Andriew, J. M., Visonneau, S., Eme, D., Tourani, J. M., Beldjord, K., Weil, M., Fernandez, E., Jaquillat, C. (1990), Changes of soluble CD16 levels in serum of HIV patients: Correlation with clinical and biological prognostic factors, J. Infect. Dis. 161, 430–435.

Kochan J., Pettine L. F., Hakimi J., Kishi K., Kinet J. P.; "Isolation of the gene coding for the alpha subunit of the human high affinity IgE receptor"; Nucleic Acids Res. 16:3584–3584(1988).

Simmons D., Seed B.; "The Fc-gamma receptor of natural killer cells is a phospholipid-linked membrane protein"; Nature 333:568–570(1988).

Kraulis, P. J. (1991), MOLSCRIPT: a program to produce both detailed and schematic plots of protein structures, J. Appl. Cryst. 24, 946–950.

Leslie, A. G. W. (1997), Mosflm user guide, mosflm version 5.50, MRC Laboratory of Molecular Biology, Cambridge, UK.

Lessel, U. and Schomburg, D. (1994), Similarities between protein 3-D structures, Protein Eng. 7, 1175–1187.

Littaua, R., Kurane, I. and Ennis, F. A. (1990), Human IgG Fc receptor II mediates antibody-dependent enhancement of dengue virus infection, J. Immunol. 144, 3183–3186.

Lynch, R. G., Hagen, M., Mueller, A., Sandor, M. (1995), Potential role of FcγR in early development of murine lymphoid cells: Evidence for functional interaction between FcγR on pre-thymocytes and an alternative, non-Ig ligand on thymic stromal cells, Immunol. Lett. 44, 105–109.

Mathiot, C., Teillaud, J. L., Elmalek, M., Mosseri, L., Euller-Ziegler, L., Daragon, A., Grosbois, B., Michaux, J. L., Facon, T., Bernard, J. F., Duclos, B., Monconduit, M., Fridman, W. H. (1993), Correlation between serum soluble CD16 (sCD16) levels and disease stage in patients with multiple myeloma, J. Clin. Immunol. 13, 41–48.

Merritt, E. A. and Murphy, M. E. P. (1994), Raster3D Version 2.0. A program for photorealistic molecular graphics, Acta Cryst. D50, 869–873.

Metzger, H. (1992A), Transmembrane signaling: The joy of aggregation, J. Immunol. 149, 1477–1487.

Metzger, H. (1992B), The receptor with high affinity for Ig E, Immunol. Rev. 125, 37–48.

Müller, S. and Hoover, R. G. (1985), T cells with Fc receptors in myeloma; suppression of growth and secretion of MOPC-315 by T alpha cells, J. Immunol. 134, 644–7.

Nicholls, A., Sharp, K. A., Honig, B. (1991), Protein folding and association: insights from the interfacial and thermodynamic properties of hydrocarbons, Proteins 11, 281–296.

Poo, H., Kraus, J. C., Mayo-Bond, L., Todd, R. F., Petty, H. R. (1995), Interaction of Fcγ receptor IIIB with complement receptor type 3 in fibroblast transfectants: evidence from lateral diffusion and resonance energy transfer studies, J. Mol. Biol. 247, 597–603.

Rappaport, E. F., Cassel, D. L., Walterhouse, D. O., McKenzie, S. E., Surrey, S., Keller, M. A., Schreiber, A. D., Schwartz, E. (1993), A soluble form of the human Fc receptor FcγRIIa: cloning, transcript analysis and detection. Exp. Hematol. 21, 689–696.

Ravanel, K., Castelle, C., Defrance, T., Wild, T. F., Charron, D., Lotteau, V., Rabourdincombe, C. (1997), Measles virus nucleocapsid protein binds to FcγRII and inhibits human B cell antibody production. J. Exp. Med. 186, 269–278.

Roman, S., Moore, J. S., Darby, C., Muller, S., Hoover, R. G. (1988), Modulation of Ig gene expression by Ig binding factors. Suppression of alpha-H chain and lambda-2-L chain mRNA accumulation in MOPC-315 by IgA-binding factor, J. Immunology 140, 3622–30.

Sarfat, D. et al., (1988), Elevation of IgE-binding factors of serum in patients with B-cell derived chronic lymphocytic leukemia. Blood, 71: 94–98.

Sauer-Eriksson, A. E., Kleywegt, G. J., Uhlen, M., Jones, T. A. (1995), Crystal structure of the C2 fragment of streptococcal protein G in complex with the Fc domain of human IgG, Structure 3, 265–78.

Small, T., et al., (1990), B-cell differentiation following autologous, conventional or T-cell depleted bone marrow transplantation: a recapitulation of normal B-cell ontogeny. Blood, 76: 1647–1656.

Sondermann, P., Huber, R., Jacob, U. (1998B), Preparation and crystallization of active soluble human FcγRIIb derived from E. coli, Protein Structure, submitted.

Sondermann, P., Kutscher, C., Jacob, U., Frey, J. (1998A), Characterization and crystallization of soluble human Fcγ receptor 11 isoforms produced in insect cells, Biochemistry, submitted.

Sondermann, P., Kutscher, C., Jacob, U., Frey, J., Analysis of complexes of IgG and soluble human Fcγ-Receptor II produced in insect cells and its crystallization, submitted.

Stengelin S., Stamenkovic I., Seed B.; "Isolation of cDNAs for two distinct human Fc receptors by ligand affinity cloning"; EMBO J. 7:1053–1059(1988).

Tax, W. J. M., Willems, H. W., Reekers, P. P. M., Capel, P. J. A., Koene, R. A. P. (1983), Polymorphism in mitogenic effect of IgG1 monoclonal antibodies against T3 antigen on human T cells, Nature 304, 445–447.

Teillaud, J. L., Brunati, S., Elmalek, M., Astier, A., Nicaise, P., Moncuit, J., Mathiot, C., Job-Desiandre, C., Fridman, W. H. (1990), Involvement of FcR+ T cells and of IgG-BF in the control of myeloma cells, Mol. Immunol. 27, 1209–17.

Turk, D. (1992), Ph.D. Thesis, TU München, Germany.

Ulvestad, E., Matre, R., Tonder, O. (1988), IgG Fc receptors in sera from patients with Rheumatoid Arthritis and Systemic Lupus Erythematosus, Scand. J. Rheumatol., Suppl. 75, 203–208.

van de Winkel, J. G. J. and Capel, P. J. A. (1993), Human IgG Fc receptor heterogeneity: Molecular aspects and clinical implications, Immunol. Today 14, 215–221.

Varin, N., Sautès, C., Galinha, A., Even, J., Hogarth, P. M., Fridman, W. H. (1989), Recombinant soluble reseptors for the Fcγ portion inhibit antibody production in vitro, Eur. J. Immunol. 19, 2263–2268.

Yang, Z., Delgado, R., Xu, L., Todd, R. F., Nabel, E. G., Sanchez, A., Nabel, G. J. (1998), Distinct cellular interactions of secreted and transmembrane Ebola virus glycoproteins, Science 279, 983–984.

Zhou, M.-J., Todd, R. F., van de Winkel, J. G. J., Petty, H. R. (1993), Cocapping of the leukoadhesin molecules complement receptor type 3 and lymphocyte function-associated antigen-1 with Fcγ receptor III on human neutrophils. Possible role of lectin-like interactions, J. Immunol. 150, 3030–3041.

---

What is claimed is:

1. A homogenous preparation of recombinant soluble FcγRIIb receptor, wherein the receptor comprises the amino acid sequence set forth in SEQ ID NO: 3, the receptor being characterized by the absence of a transmembrane domain, signal peptide and glycosylation, the said preparation being obtainable by expression of a nucleic acid encoding such receptor in prokaryotes under conditions that lead to production of insoluble inclusion bodies and renaturation of the receptor molecules from the inclusion bodies.

2. The homogenous preparation of claim 1, wherein the receptor is of human origin.

* * * * *

SEQUENCE LISTING

```
<160> NUMBER OF SEQ ID NOS: 18

<210> SEQ ID NO 1
<211> LENGTH: 269
<212> TYPE: PRT
<213> ORGANISM: Homo sapiens

<400> SEQUENCE: 1

Met Ala Val Ile Ser Leu Gln Pro Pro Trp Val Ser Val Phe Gln Glu
 1               5                  10                  15

Glu Thr Val Thr Leu His Cys Glu Val Leu His Leu Pro Gly Ser Ser
                20                  25                  30

Ser Thr Gln Trp Phe Leu Asn Gly Thr Ala Thr Gln Thr Ser Thr Pro
            35                  40                  45

Ser Tyr Arg Ile Thr Ser Ala Ser Val Asn Asp Ser Gly Glu Tyr Arg
        50                  55                  60

Cys Gln Arg Gly Leu Ser Gly Arg Ser Asp Pro Ile Gln Leu Glu Ile
 65                  70                  75                  80

His Arg Gly Trp Leu Leu Leu Gln Val Ser Ser Arg Val Phe Thr Glu
                85                  90                  95
```

-continued

```
Gly Glu Pro Leu Ala Leu Arg Cys His Ala Trp Lys Asp Lys Leu Val
            100                 105                 110

Tyr Asn Val Leu Tyr Tyr Arg Asn Gly Lys Ala Phe Lys Phe Phe His
            115                 120                 125

Trp Asn Ser Asn Leu Thr Ile Leu Lys Thr Asn Ile Ser His Asn Gly
        130                 135                 140

Thr Tyr His Cys Ser Gly Met Gly Lys His Arg Tyr Thr Ser Ala Gly
145                 150                 155                 160

Ile Ser Val Thr Val Lys Glu Leu Phe Pro Ala Pro Val Leu Asn Ala
                165                 170                 175

Ser Val Thr Ser Pro Leu Leu Glu Gly Asn Leu Val Thr Leu Ser Cys
            180                 185                 190

Glu Thr Lys Leu Leu Leu Gln Arg Pro Gly Leu Gln Leu Tyr Phe Ser
        195                 200                 205

Phe Tyr Met Gly Ser Lys Thr Leu Arg Gly Arg Asn Thr Ser Ser Glu
    210                 215                 220

Tyr Gln Ile Leu Thr Ala Arg Arg Glu Asp Ser Gly Leu Tyr Trp Cys
225                 230                 235                 240

Glu Ala Ala Thr Glu Asp Gly Asn Val Leu Lys Arg Ser Pro Glu Leu
                245                 250                 255

Glu Leu Gln Val Leu Gly Leu Gln Leu Pro Thr Pro Val
            260                 265
```

<210> SEQ ID NO 2
<211> LENGTH: 174
<212> TYPE: PRT
<213> ORGANISM: Homo sapiens

<400> SEQUENCE: 2

```
Met Ala Ala Pro Pro Lys Ala Val Leu Lys Leu Glu Pro Pro Trp Ile
  1               5                  10                  15

Asn Val Leu Gln Glu Asp Ser Val Thr Leu Thr Cys Gln Gly Ala Arg
            20                  25                  30

Ser Pro Glu Ser Asp Ser Ile Gln Trp Phe His Asn Gly Asn Leu Ile
        35                  40                  45

Pro Thr His Thr Gln Pro Ser Tyr Arg Phe Lys Ala Asn Asn Asn Asp
    50                  55                  60

Ser Gly Glu Tyr Thr Cys Gln Thr Gly Gln Thr Ser Leu Ser Asp Pro
65                  70                  75                  80

Val His Leu Thr Val Leu Ser Glu Trp Leu Val Leu Gln Thr Pro His
                85                  90                  95

Leu Glu Phe Gln Glu Gly Glu Thr Ile Met Leu Arg Cys His Ser Trp
            100                 105                 110

Lys Asp Lys Pro Leu Val Lys Val Thr Phe Phe Gln Asn Gly Lys Ser
        115                 120                 125

Gln Lys Phe Ser Arg Leu Asp Pro Thr Phe Ser Ile Pro Gln Ala Asn
    130                 135                 140

His Ser His Ser Gly Asp Tyr His Cys Thr Gly Asn Ile Gly Tyr Thr
145                 150                 155                 160

Leu Phe Ser Ser Lys Pro Val Thr Ile Thr Val Gln Val Pro
                165                 170
```

<210> SEQ ID NO 3
<211> LENGTH: 185
<212> TYPE: PRT
<213> ORGANISM: Homo sapiens

<400> SEQUENCE: 3

```
Met Gly Thr Pro Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
                20                  25                  30

Gly Thr His Ser Pro Glu Ser Asp Ser Ile Gln Trp Phe His Asn Gly
            35                  40                  45

Asn Leu Ile Pro Thr His Thr Gln Pro Ser Tyr Arg Phe Lys Ala Asn
        50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
            100                 105                 110

His Ser Trp Lys Asp Lys Pro Leu Val Lys Val Thr Phe Phe Gln Asn
            115                 120                 125

Gly Lys Ser Lys Lys Phe Ser Arg Ser Asp Pro Asn Phe Ser Ile Pro
        130                 135                 140

Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Ser Pro Met Gly Ile Ile
            180                 185
```

<210> SEQ ID NO 4
<211> LENGTH: 176
<212> TYPE: PRT
<213> ORGANISM: Homo sapiens

<400> SEQUENCE: 4

```
Met Arg Thr Glu Asp Leu Pro Lys Ala Val Val Phe Leu Glu Pro Gln
1               5                   10                  15

Trp Tyr Ser Val Leu Glu Lys Asp Ser Val Thr Leu Lys Cys Gln Gly
                20                  25                  30

Ala Tyr Ser Pro Glu Asp Asn Ser Thr Gln Trp Phe His Asn Glu Ser
            35                  40                  45

Leu Ile Ser Ser Gln Ala Ser Ser Tyr Phe Ile Asp Ala Ala Thr Val
        50                  55                  60

Asn Asp Ser Gly Glu Tyr Arg Cys Gln Thr Asn Leu Ser Thr Leu Ser
65                  70                  75                  80

Asp Pro Val Gln Leu Glu Val His Ile Gly Trp Leu Leu Leu Gln Ala
                85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
            115                 120                 125

Lys Asp Arg Lys Tyr Phe His His Asn Ser Asp Phe His Ile Pro Lys
        130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Asn Ile Thr Ile Thr Gln Gly
                165                 170                 175
```

<210> SEQ ID NO 5
<211> LENGTH: 183
<212> TYPE: PRT
<213> ORGANISM: Homo sapiens

<400> SEQUENCE: 5

Met Ala Val Pro Gln Lys Pro Lys Val Ser Leu Asn Pro Pro Trp Asn
1               5                   10                  15

Arg Ile Phe Lys Gly Glu Asn Val Thr Leu Thr Cys Asn Gly Asn Asn
                20                  25                  30

Phe Phe Glu Val Ser Ser Thr Lys Trp Phe His Asn Gly Ser Leu Ser
            35                  40                  45

Glu Glu Thr Asn Ser Ser Leu Asn Ile Val Asn Ala Lys Phe Glu Asp
        50                  55                  60

Ser Gly Glu Tyr Lys Cys Gln His Gln Gln Val Asn Glu Ser Glu Pro
65                  70                  75                  80

Val Tyr Leu Glu Val Phe Ser Asp Trp Leu Leu Leu Gln Ala Ser Ala
                85                  90                  95

Glu Val Val Met Glu Gly Gln Pro Leu Phe Leu Arg Cys His Gly Trp
            100                 105                 110

Arg Asn Trp Asp Val Tyr Lys Val Ile Tyr Tyr Lys Asp Gly Glu Ala
        115                 120                 125

Leu Lys Tyr Trp Tyr Glu Asn His Asn Ile Ser Ile Thr Asn Ala Thr
    130                 135                 140

Val Glu Asp Ser Gly Thr Tyr Tyr Cys Thr Gly Lys Val Trp Gln Leu
145                 150                 155                 160

Asp Tyr Glu Ser Glu Pro Leu Asn Ile Thr Val Ile Lys Ala Pro Arg
                165                 170                 175

Glu Lys Tyr Trp Leu Gln Phe
            180

<210> SEQ ID NO 6
<211> LENGTH: 275
<212> TYPE: PRT
<213> ORGANISM: Homo sapiens

<400> SEQUENCE: 6

Met Asp Thr Thr Gln Ser Leu Lys Gln Leu Glu Glu Arg Ala Ala Arg
1               5                   10                  15

Asn Val Ser Gln Val Ser Lys Asn Leu Glu Ser His His Gly Asp Gln
                20                  25                  30

Met Thr Gln Lys Ser Gln Ser Thr Gln Ile Ser Gln Glu Leu Glu Glu
            35                  40                  45

Leu Arg Ala Glu Gln Gln Arg Leu Lys Ser Gln Asp Leu Glu Leu Ser
        50                  55                  60

Trp Asn Leu Asn Gly Leu Gln Ala Asp Leu Ser Ser Phe Lys Ser Gln
65                  70                  75                  80

Glu Leu Asn Glu Arg Asn Glu Ala Ser Asp Leu Leu Glu Arg Leu Arg
                85                  90                  95

Glu Glu Val Thr Lys Leu Arg Met Glu Leu Gln Val Ser Ser Gly Phe
            100                 105                 110

Val Cys Asn Thr Cys Pro Glu Lys Trp Ile Asn Phe Gln Arg Lys Cys
        115                 120                 125

Tyr Tyr Phe Gly Lys Gly Thr Lys Gln Trp Val His Ala Arg Tyr Ala
    130                 135                 140

-continued

```
Cys Asp Asp Met Glu Gly Gln Leu Val Ser Ile His Ser Pro Glu Glu
145                 150                 155                 160

Gln Asp Phe Leu Thr Lys His Ala Ser His Thr Gly Ser Trp Ile Gly
            165                 170                 175

Leu Arg Asn Leu Asp Leu Lys Gly Glu Phe Ile Trp Val Asp Gly Ser
            180                 185                 190

His Val Asp Tyr Ser Asn Trp Ala Pro Gly Glu Pro Thr Ser Arg Ser
            195                 200                 205

Gln Gly Glu Asp Cys Val Met Met Arg Gly Ser Gly Arg Trp Asn Asp
    210                 215                 220

Ala Phe Cys Asp Arg Lys Leu Gly Ala Trp Val Cys Asp Arg Leu Ala
225                 230                 235                 240

Thr Cys Thr Pro Pro Ala Ser Glu Gly Ser Ala Glu Ser Met Gly Pro
                245                 250                 255

Asp Ser Arg Pro Asp Pro Asp Gly Arg Leu Pro Thr Pro Ser Ala Pro
            260                 265                 270

Leu His Ser
        275
```

<210> SEQ ID NO 7
<211> LENGTH: 820
<212> TYPE: DNA
<213> ORGANISM: Homo sapiens

<400> SEQUENCE: 7

```
catatggcag tgatctcttt gcagcctcca tgggtcagcg tgttccaaga ggaaaccgta      60
accttgcact gtgaggtgct ccatctgcct gggagcagct ctacacagtg gtttctcaat     120
ggcacagcca ctcagacctc gaccccagc tacagaatca cctctgccag tgtcaatgac     180
agtggtgaat acaggtgcca gagaggtctc tcagggcgaa gtgaccccat acagctggaa     240
atccacagag gctggctact actgcaggtc tccagcagag tcttcacgga aggagaacct     300
ctggccttga ggtgtcatgc gtggaaggat aagctggtgt acaatgtgct ttactatcga     360
aatggcaaag cctttaagtt tttccactgg aattctaacc tcaccattct gaaaaccaac     420
ataagtcaca atggcaccta ccattgctca ggcatgggaa agcatcgcta cacatcagca     480
ggaatatctg tcactgtgaa agagctattt ccagctccag tgctgaatgc atctgtgaca     540
tccccactcc tggagggaa tctggtcacc ctgagctgtg aaacaaagtt gctcttgcag     600
aggcctggtt tgcagcttta cttctccttc tacatgggca gcaagaccct gcgaggcagg     660
aacacatcct ctgaatacca atactaact gctagaagag aagactctgg gttatactgg     720
tgcgaggctg ccacagagga tggaaatgtc cttaagcgca gccctgagtt ggagcttcaa     780
gtgcttggcc tccagttacc aactcctgtc tagtctcgag                           820
```

<210> SEQ ID NO 8
<211> LENGTH: 533
<212> TYPE: DNA
<213> ORGANISM: Homo sapiens

<400> SEQUENCE: 8

```
catatggcag ctcccccaaa ggctgtgctg aaacttgagc cccgtggat caacgtgctc       60
caggaggact ctgtgactct gacatgccag ggggctcgca gccctgagag cgactccatt     120
cagtggttcc acaatgggaa tctcattccc acccacacgc agcccagcta caggttcaag     180
gccaacaaca atgacagcgg ggagtacacg tgccagactg ccagaccag cctcagcgac     240
```

```
cctgtgcatc tgactgtgct ttccgaatgg ctggtgctcc agacccctca cctggagttc    300
caggagggag aaaccatcat gctgaggtgc cacagctgga aggacaagcc tctggtcaag    360
gtcacattct tccagaatgg aaaatcccag aaattctccc gtttggatcc caccttctcc    420
atcccacaag caaaccacag tcacagtggt gattaccact gcacaggaaa cataggctac    480
acgctgttct catccaagcc tgtgaccatc actgtccaag tgccctgaag ctt           533
```

<210> SEQ ID NO 9
<211> LENGTH: 569
<212> TYPE: DNA
<213> ORGANISM: Homo sapiens

<400> SEQUENCE: 9

```
ccatggggac acctgcagct cccccaaagg ctgtgctgaa actcgagccc cagtggatca     60
acgtgctcca ggaggactct gtgactctga catgccgggg gactcacagc cctgagagcg    120
actccattca gtggttccac aatgggaatc tcattcccac ccacacgcag cccagctaca    180
ggttcaaggc caacaacaat gacagcgggg agtacacgtg ccagactggc cagaccagcc    240
tcagcgaccc tgtgcatctg actgtgcttt ctgagtggct ggtgctccag accccctcacc   300 tggagttcca ggagggagaa accatcgtgc tgaggtgcca cagctggaag gacaagcctc    360
tggtcaaggt cacattcttc cagaatggaa atccaagaa attttcccgt tcggatccca    420
acttctccat cccacaagca aaccacagtc acagtggtga ttaccactgc acaggaaaca    480
taggctacac gctgtactca tccaagcctg tgaccatcac tgtccaagct cccagctctt    540
caccgatggg gatcatttag gctgtcgac                                       569
```

<210> SEQ ID NO 10
<211> LENGTH: 538
<212> TYPE: DNA
<213> ORGANISM: Homo sapiens

<400> SEQUENCE: 10

```
catatgcgga ctgaagatct cccaaaggct gtggtgttcc tggagcctca atggtacagc     60
gtgcttgaga aggacagtgt gactctgaag tgccagggag cctactcccc tgaggacaat    120
tccacacagt ggtttcacaa tgagagcctc atctcaagcc aggcctcgag ctacttcatt    180
gacgctgcca cagtcaacga cagtggagag tacaggtgcc agacaaacct ctccacccta    240
agtgacccgg tgcagctaga agtccatatc ggctggctgt tgctccaggc ccctcggtgg    300
gtgttcaagg aggaagaccc tattcacctg aggtgtcaca gctggaagaa cactgctctg    360
cataaggtca catatttaca gaatggcaaa gacaggaagt attttcatca taattctgac    420
ttccacattc caaaagccac actcaaagat agcggctcct acttctgcag ggggcttgtt    480
gggagtaaaa atgtgtcttc agagactgtg aacatcacca tcactcaagg ttaagctt     538
```

<210> SEQ ID NO 11
<211> LENGTH: 560
<212> TYPE: DNA
<213> ORGANISM: Homo sapiens

<400> SEQUENCE: 11

```
catatggcag tccctcagaa acctaaggtc tccttgaacc ctccatggaa tagaatattt     60
aaaggagaga atgtgactct acatgtaat gggaacaatt tctttgaagt cagttccacc    120
aaatggttcc acaatggcag cctttcagaa gagacaaatt caagtttgaa tattgtgaat    180
```

```
gccaaatttg aagacagtgg agaatacaaa tgtcagcacc aacaagttaa tgagagtgaa    240
cctgtgtacc tggaagtctt cagtgactgg ctgctccttc aggcctctgc tgaggtggtg    300
atggagggcc agcccctctt cctcaggtgc catggttgga ggaactggga tgtgtacaag    360
gtgatctatt ataaggatgg tgaagctctc aagtactggt atgagaacca caacatctcc    420
attacaaatg ccacagttga agacagtgga acctactact gtacgggcaa agtgtggcag    480
ctggactatg agtctgagcc cctcaacatt actgtaataa agctccgcg tgagaagtac    540 tggctacaat tttaggatcc                                                560

<210> SEQ ID NO 12
<211> LENGTH: 532
<212> TYPE: DNA
<213> ORGANISM: Homo sapiens

<400> SEQUENCE: 12
catatggagt tgcaggtgtc cagcggcttt gtgtgcaaca cgtgccctga aaagtggatc     60
aatttccaac ggaagtgcta ctacttcggc aagggcacca gcagtgggt ccacgcccgg    120 tatgcctgtg acgacatgga agggcagctg gtcagcatcc acagcccgga ggagcaggac    180
ttcctgacca agcatgccag ccacaccggc tcctggattg ccttcggaa cttggacctg    240 aagggggagt ttatctgggt ggatgggagc cacgtggact acagcaactg gctccaggg    300 gagcccacca gccggagcca gggcgaggac tgcgtgatga tgcggggctc cggtcgctgg    360
aacgacgcct tctgcgaccg taagctgggc gcctgggtgt cgaccggct ggccacatgc    420 acgccgccag ccagcgaagg ttccgcggag tccatgggac ctgattcaag accagaccct    480
gacggccgcc tgcccacccc ctctgccct ctccactctt gagcatggat cc             532

<210> SEQ ID NO 13
<211> LENGTH: 1419
<212> TYPE: DNA
<213> ORGANISM: Homo sapiens

<400> SEQUENCE: 13
ggctgtgact gctgtgctct gggcgccact cgctccaggg agtgatggga atcctgtcat     60
ttttacctgt ccttgccact gagagtgact gggctgactg caagtccccc cagccttggg    120
gtcatatgct tctgtggaca gctgtgctat tcctggctcc tgttgctggg acacctgcag    180
ctcccccaaa ggctgtgctg aaactcgagc cccagtggat caacgtgctc caggaggact    240
ctgtgactct gacatgccgg gggactcaca gccctgagag cgactccatt cagtggttcc    300
acaatgggaa tctcattccc acccacacgc agcccagcta caggttcaag gccaacaaca    360
atgacagcgg ggagtacacg tgccagactg gccagaccag cctcagcgac cctgtgcatc    420
tgacagtgct ttctgagtgg ctggtgctcc agaccctca cctggagttc caggagggag    480
aaaccatcgt gctgaggtgc acagctggaa ggacaagcc tctggtcaag gtcacattct    540
tccagaatgg aaaatccaag aaattttccc gttcggatcc caacttctcc atcccacaag    600
caaaccacag tcacagtggt gattaccatt gcacaggaaa cataggctac acgctgtact    660
catccaagcc tgtgaccatc actgtccaag ctcccagctc ttcaccgatg gggatcattg    720
tggctgtggt cactgggatt gctgtagctg ccattgttgc tgctgtagtg gccttgatct    780
actgcaggaa aaagcggatt tcagccaatc ccactaatcc tgatgaggct gacaaagttg    840
gggctgagaa cacaatcacc tattcacttc tcatgcaccc ggatgctctg aagagcctg    900 atgaccagaa ccgtatttag tctccattgt cttgcattgg gatttgagaa gaaatcagag    960
```

-continued

```
agggaagatc tggtatttcc tggcctaaat tccccttggg gaggacaggg agatgctgca    1020
gttccaaaag agaaggtttc ttccagagtc atctacctga gtcctgaagc tccctgtcct    1080
gaaagccaca gacaatatgg tcccaaatgc ccgactgcac cttctgtgct tcagctcttc    1140
ttgacatcaa ggctcttccg ttccacatcc acacagccaa tccaattaat caaaccactg    1200
ttattaacag ataatagcaa cttgggaaat gctatgtta caggttacgt gagaacaatc     1260
atgtaaatct atatgatttc agaaatgtta aaatagacta acctctacca gcacattaaa    1320
agtgattgtt tctgggtgat aaaattattg atgattttta ttttctttat ttttctataa    1380
agatcatata ttacttttat aataaaacat tataaaaac                           1419
```

<210> SEQ ID NO 14
<211> LENGTH: 1068
<212> TYPE: DNA
<213> ORGANISM: Homo sapiens

<400> SEQUENCE: 14

```
agatctcagc acagtaagca ccaggagtcc atgaagaaga tggctcctgc catggaatcc      60
cctactctac tgtgtgtagc cttactgttc ttcgctccag atggcgtgtt agcagtccct     120
cagaaaccta aggtctcctt gaaccctcca tggaatagaa tatttaaagg agagaatgtg    180
actcttacat gtaatgggaa caatttcttt gaagtcagtt ccaccaaatg gttccacaat    240
ggcagccttt cagaagagac aaattcaagt ttgaatattg tgaatgccaa atttgaagac    300
agtggagaat acaaatgtca gcaccaacaa gttaatgaga gtgaacctgt gtacctggaa    360
gtcttcagtg actggctgct ccttcaggcc tctgctgagg tggtgatgga gggccagccc    420
ctcttcctca ggtgccatgg ttggaggaac tgggatgtgt acaaggtgat ctattataag    480
gatggtgaag ctctcaagta ctggtatgag aaccacaaca tctccattac aaatgccaca    540
gttgaagaca gtgaaccta ctactgtacg ggcaaagtgt ggcagctgga ctatgagtct    600
gagcccctca acattactgt aataaaagct ccgcgtgaga agtactggct acaattttttt    660 atcccattgt tggtggtgat tctgtttgct gtggacacag gattatttat ctcaactcag    720
cagcaggtca catttctctt gaagattaag agaaccagga aaggcttcag acttctgaac    780
ccacatccta agccaaaccc caaaaacaac tgatataatt aactcaagaa atatttgcaa    840
cattagtttt tttccagcat cagcaattgc tactcaattg tcaaacacag cttgcaatat    900
acatagaaac gtctgtgctc aaggatttat agaaatgctt cattaaactg agtgaaactg    960
attaagtggc atgtaatagt aagtgctcaa ttaacattgg ttgaataaat gagagaatga    1020
atagattcat ttattagcat ttgtaaaaga gatgttcaat ttagatct                 1068
```

<210> SEQ ID NO 15
<211> LENGTH: 1321
<212> TYPE: DNA
<213> ORGANISM: Homo sapiens

<400> SEQUENCE: 15

```
gacagatttc actgctccca ccagcttgga gacaacatgt ggttcttgac aactctgctc     60
ctttgggttc cagttgatgg gcaagtggac accacaaagg cagtgatctc tttgcagcct    120
ccatgggtca gcgtgttcca agaggaaacc gtaaccttgc actgtgaggt gctccatctg    180
cctgggagca gctctacaca gtggtttctc aatggcacag ccactcagac ctcgacccccc    240 agctacagaa tcacctctgc cagtgtcaat gacagtggtg aatacaggtg ccagagaggt    300
```

-continued

```
ctctcagggc gaagtgaccc catacagctg gaaatccaca gaggctggct actactgcag    360
gtctccagca gagtcttcac ggaaggagaa cctctggcct tgaggtgtca tgcgtggaag    420
gataagctgg tgtacaatgt gctttactat cgaaatggca agcctttaa gttttttccac    480 tggaattcta acctcaccat tctgaaaacc aacataagtc acaatggcac ctaccattgc    540
tcaggcatgg gaaagcatcg ctacacatca gcaggaatat ctgtcactgt gaaagagcta    600
tttccagctc cagtgctgaa tgcatctgtg acatccccac tcctggaggg gaatctggtc    660
accctgagct gtgaaacaaa gttgctcttg cagaggcctg gtttgcagct ttacttctcc    720
ttctacatgg gcagcaagac cctgcgaggc aggaacacat cctctgaata ccaaatacta    780
actgctagaa gagaagactc tgggttatac tggtgcgagg ctgccacaga ggatggaaat    840
gtccttaagc gcagccctga gttggagctt caagtgcttg gcctccagtt accaactcct    900
gtctggtttc atgtcctttt ctatctggca gtgggaataa tgtttttagt gaacactgtt    960
ctctgggtga caatacgtaa agaactgaaa agaaagaaaa agtgggattt agaaatctct   1020
ttggattctg gtcatgagaa gaaggtaact tccagccttc aagaagacag acatttagaa   1080
gaagagctga aatgtcagga acaaaaagaa gaacagctgc aggaagggt gcaccggaag   1140 gagccccagg gggccacgta gcagcggctc agtgggtggc catcgatctg accgtcccc    1200 tgcccacttg ctccccgtga gcactgcgta caaacatcca aaagttcaac aacaccagaa   1260
ctgtgtgtct catggtatgt aactcttaaa gcaaataaat gaactgactt caaaaaaaaa   1320
a                                                                  1321
```

<210> SEQ ID NO 16
<211> LENGTH: 2359
<212> TYPE: DNA
<213> ORGANISM: Homo sapiens

<400> SEQUENCE: 16

```
cccaaatgtc tcagaatgta tgtcccagaa acctgtggct gcttcaacca ttgacagttt     60
tgctgctgct ggcttctgca gacagtcaag ctgcagctcc cccaaaggct gtgctgaaac    120
ttgagccccc gtggatcaac gtgctccagg aggactctgt gactctgaca tgccaggggg    180
ctcgcagccc tgagagcgac tccattcagt ggttccacaa tgggaatctc attcccaccc    240
acacgcagcc cagctacagg ttcaaggcca acaacaatga cagcggggag tacacgtgcc    300
agactggcca gaccagcctc agcgaccctg tgcatctgac tgtgctttcc gaatggctgg    360
tgctccagac ccctcacctg gagttccagg agggagaaac catcatgctg aggtgccaca    420
gctggaagga caagcctctg gtcaaggtca cattcttcca gaatggaaaa tcccagaaat    480
tctcccgttt ggatcccacc ttctccatcc acaagcaaa ccacagtcac agtggtgatt    540
accactgcac aggaaacata ggctacacgc tgttctcatc caagcctgtg accatcactg    600
tccaagtgcc cagcatgggc agctcttcac caatggggat cattgtggct gtggtcattg    660
cgactgctgt agcagccatt gttgctgctg tagtggcctt gatctactgc aggaaaaagc    720
ggatttcagc caattccact gatcctgtga aggctgccca atttgagcca cctgacgtc    780 aaatgattgc catcagaaag agacaacttg aagaaccaa caatgactat gaaacagctg    840
acggcggcta catgactctg aaccccaggg cacctactga cgatgataaa acatctaccc    900
tgactcttcc tcccaacgac catgtcaaca gtaataacta agagtaacg ttatgccatg    960 tggtcatact ctcagcttgc tgatggatga caaaagagg ggaattgtta aaggaaaatt   1020
taaatggaga ctggaaaaat cctgagcaaa caaaaccacc tggcccttag aaatagcttt   1080
```

```
aactttgctt aaactacaaa cacaagcaaa acttcacggg gtcatactac atacaagcat    1140
aagcaaaact taacttggat catttctggt aaatgcttat gttagaaata agacaacccc    1200
agccaatcac aagcagccta ctaacatata attaggtgac tagggacttt ctaagaagat    1260
acctaccccc aaaaaacaat tatgtaattg aaaaccaacc gattgccttt attttgcttc    1320
cacattttcc caataaatac ttgcctgtga cattttgcca ctggaacact aaacttcatg    1380
aattgcgcct cagatttttc ctttaacatc ttttttttt ttgacagagt ctcaatctgt    1440
tacccaggct ggagtgcagt ggtgctatct tggctcactg caaacccgcc tcccaggttt    1500
aagcgattct tatgcctcag cctcccagta gctgggatta gaggcatgtg ccatcatacc    1560
cagctaattt ttgtattttt tattttttat tttagtaga acagggtttt cgcaatgttg    1620
gccaggccga tctcgaactt ctggcctcta gcgatctgcc cgcctcggcc tcccaaagtg    1680
ctgggatgac cgcatcagcc ccaatgtcca gcctctttaa catcttcttt cctatgccct    1740
ctctgtggat ccctactgct ggtttctgcc ttctccatgc tgagaacaaa atcacctatt    1800
cactgcttat gcagtcggaa gctccagaag aacaaagagc ccaattacca gaaccacatt    1860
aagtctccat tgttttgcct tgggatttga gaagagaatt agagaggtga ggatctggta    1920
tttcctggac taaattccct tggggaagac gaagggatgc tgcagttcca aaagagaagg    1980
actcttccag agtcatctac ctgagtccca aagctccctg tcctgaaagc cacagacaat    2040
atggtcccaa atgactgact gcaccttctg tgcctcagcc gttcttgaca tcaagaatct    2100
tctgttccac atccacacag ccaatacaat tagtcaaacc actgttatta acagatgtag    2160
caacatgaga aacgcttatg ttacaggtta catgagagca atcatgtaag tctatatgac    2220
ttcagaaatg ttaaaataga ctaacctcta acaacaaatt aaaagtgatt gtttcaaggt    2280
gatgcaatta ttgatgacct attttatttt tctataatga tcatatatta cctttgtaat    2340
aaaacattat aaccaaaac                                                 2359

<210> SEQ ID NO 17
<211> LENGTH: 887
<212> TYPE: DNA
<213> ORGANISM: Homo sapiens

<400> SEQUENCE: 17
tctttggtga cttgtccact ccagtgtggc atcatgtggc agctgctcct cccaactgct      60
ctgctacttc tagtttcagc tggcatgcgg actgaagatc tcccaaaggc tgtggtgttc     120
ctggagcctc aatggtacag cgtgcttgag aaggacagtg tgactctgaa gtgccaggga     180
gcctactccc ctgaggacaa ttccacacag tggtttcaca atgagagcct catctcaagc     240
caggcctcga gctacttcat tgacgctgcc acagtcaacg acagtggaga gtacaggtgc     300
cagacaaacc tctccaccct cagtgacccg gtgcagctag aagtccatat cggctggctg     360
ttgctccagg cccctcggtg ggtgttcaag gaggaagacc ctattcacct gaggtgtcac     420
agctggaaga acactgctct gcataaggtc acatatttac agaatggcaa agacaggaag     480
tattttcatc ataattctga cttccacatt ccaaaagcca cactcaaaga tagcggctcc     540
tacttctgca gggggcttgt tgggagtaaa aatgtgtctt cagagactgt gaacatcacc     600
atcactcaag gtttggcagt gtcaaccatc tcatcattct ctccacctgg gtaccaagtc     660
tctttctgct tggtgatggt actccttttt gcagtggaca caggactata tttctctgtg     720
aagacaaaca tttgaagctc aacaagagac tggaaggacc ataaacttaa atggagaaag     780
```

-continued

```
gaccctcaag acaaatgacc cccatcccat gggagtaata agagcagtgg cagcagcatc      840
tctgaacatt tctctggatt tgcaacccca tcatcctcag gcctctc                    887
```

<210> SEQ ID NO 18
<211> LENGTH: 1503
<212> TYPE: DNA
<213> ORGANISM: Homo sapiens

<400> SEQUENCE: 18

```
ctcctgctta aacctctgtc tctgacggtc cctgccaatc gctctggtcg accccaacac       60
actaggagga cagacacagg ctccaaactc cactaagtga ccagagctgt gattgtgccc      120
gctgagtgga ctgcgttgtc agggagtgag tgctccatca tcgggagaat ccaagcagga      180
ccgccatgga ggaaggtcaa tattcagaga tcgaggagct tcccaggagg cggtgttgca      240
ggcgtgggac tcagatcgtg ctgctgggc tggtgaccgc cgctctgtgg gctgggctgc       300
tgactctgct tctcctgtgg cactgggaca ccacacagag tctaaaacag ctggaagaga      360
gggctgcccg gaacgtctct caagtttcca agaacttgga aagccaccac ggtgaccaga      420
tggcgcagaa atcccagtcc acgcagattt cacaggaact ggaggaactt cgagctgaac      480
agcagagatt gaaatctcag gacttggagc tgtcctggaa cctgacggg cttcaagcag       540
atctgagcag cttcaagtcc caggaattga acgagaggaa cgaagcttca gatttgctgg      600
aaagactccg ggaggaggtg acaaagctaa ggatggagtt gcaggtgtcc agcggctttg      660
tgtgcaacac gtgccctgaa aagtggatca atttccaacg gaagtgctac tacttcggca      720
agggcaccaa gcagtgggtc cacgcccggt atgcctgtga cgacatggaa gggcagctgg      780
tcagcatcca cagcccggag gagcaggact tcctgaccaa gcatgccagc cacaccggct      840
cctggattgg ccttcggaac ttggacctga agggagagtt tatctgggtg gatgggagcc      900
atgtggacta cagcaactgg gctccagggg agcccaccag ccggagccag ggcgaggact      960
gcgtgatgat gcgggctcc ggtcgctgga acgacgcctt ctgcgaccgt aagctgggcg      1020
cctgggtgtg cgaccggctg gccacatgca cgccgccagc cagcgaaggt tccgcggagt     1080
ccatgggacc tgattcaaga ccagaccctg acggccgcct gcccaccccc tctgccctc      1140
tccactcttg agcatggata cagccaggcc cagagcaaga ccctgaagac ccccaaccac     1200
ggcctaaaag cctctttgtg gctgaaaggt ccctgtgaca tttctgcca cccaaacgga      1260
ggcagctgac acatctcccg ctcctctatg gcccctgcct tcccaggagt acaccccaac     1320
agcaccctct ccagatggga gtgccccaa cagcaccctc tccagatgag agtacacccc     1380
aacagcaccc tctccagatg cagcccccatc tcctcagcac cccaggacct gagtatcccc     1440
agctcaggtg gtgagtcctc ctgtccagcc tgcatcaata aaatgggca gtgatggcct      1500
ccc                                                                    1503
```